United States Patent [19]

Wissner

[11] 4,209,639

[45] Jun. 24, 1980

[54] 13-THIA-PROSTAGLANDINS

[75] Inventor: Allan Wissner, Monsey, N.Y.

[73] Assignee: American Cyanamid Company, Stamford, Conn.

[21] Appl. No.: 615,274

[22] Filed: Sep. 22, 1975

[51] Int. Cl.$^2$ ............... C07C 177/00; C07C 149/26; C07C 149/40
[52] U.S. Cl. ................... 562/426; 260/399; 260/348.57; 560/9; 560/121; 560/231; 562/503; 568/649; 568/657; 568/62; 568/63; 424/305; 424/308; 424/317; 549/15
[58] Field of Search ............... 260/516, 470; 560/9; 562/426

[56] References Cited

U.S. PATENT DOCUMENTS

| | | | |
|---|---|---|---|
| 3,932,487 | 1/1976 | Kramer et al. | 260/516 |
| 3,985,798 | 10/1976 | Floyd, Jr. et al. | 260/516 |
| 4,016,184 | 5/1977 | Morton | 260/408 |
| 4,018,820 | 5/1977 | Fried | 260/514 |
| 4,080,458 | 3/1978 | Radunz et al. | 424/263 |

FOREIGN PATENT DOCUMENTS 828925 10/1975 Belgium ................... 260/516

*Primary Examiner*—Robert Gerstl
*Attorney, Agent, or Firm*—Richard J. Hammond

[57] ABSTRACT

This disclosure describes novel 13-thia prostanoic acids and derivatives thereof useful in causing prostaglandin-like biological responses.

8 Claims, No Drawings

13-THIA-PROSTAGLANDINS

BRIEF SUMMARY OF THE INVENTION

This invention relates to novel 13-thiaprostanoic acids and their derivatives and intermediates for their preparation. The novel 13-thia derivatives may be represented by the following general formula, and all optical antipodes, racemic and diastereomeric mixtures thereof:

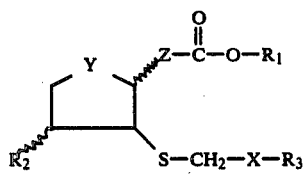

wherein $R_1$ is selected from the group consisting of hydrogen and a branched or straight chain alkyl group of 1 to 12 carbon atoms; $R_2$ is selected from the group consisting of hydrogen, hydroxy, and lower alkanoyloxy; $R_3$ is selected from the group consisting of hydrogen, alkyl group of 4 to 7 carbon atoms, or a phenoxymethyl group in which the phenyl ring is optionally substituted with one or two radicals selected from the group consisting of halogen, trifluoromethyl, lower alkyl, and lower alkoxy radicals; X is a divalent radical selected from the group consisting of

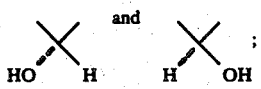

Y is a divalent radical selected from the group consisting of

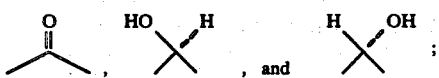

Z is a divalent radical selected from the group consisting of those of the formulae:

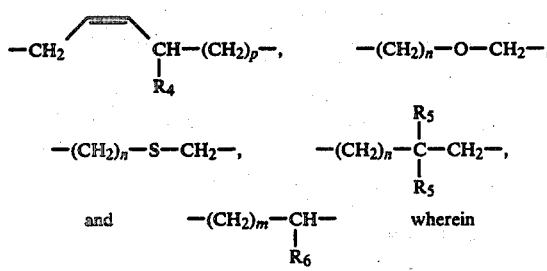

$R_4$ is selected from the group consisting of hydrogen or lower alkyl groups of 1 to 3 carbon atoms; $R_5$ is a lower alkyl group of 1 to 3 carbon atoms; $R_6$ is a lower alkyl group of 1 to 3 carbon atoms or a phenyl ring; p is an integer having the values 2 to 5, inclusive; n is an integer having the values 3 to 6, inclusive; m is an integer having the values 4 to 7, inclusive; and wherein the moiety of the formula:

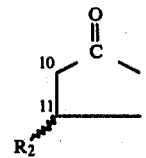

may be the divalent radical of the formula:

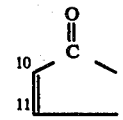

with the proviso that when $R_1$ is a substituted or unsubstituted phenoxymethyl group, Z also may be represented by the formula: $-(CH_2)_q-$ wherein q is a integer with the values 5 to 8, inclusive. Also embraced by the present invention are the non-toxic, pharmaceutically-acceptable salts of the novel compounds of the present invention when $R_3$ is hydrogen. The cations comprised in these salts include, for example, the non-toxic metal cations such as the sodium ion, potassium ion, calcium ion, and magnesium ion as well as the organic amine cations such as the tri(lower alkyl) amine cations (e.g. tri-ethylamine), procaine, and the like.

The novel compounds of the present invention are obtainable as yellow oils having characteristic absorption spectra. They are relatively insoluble in water but are relatively soluble in common organic solvents such as ethanol, ethylacetate, dimethylformamide, and the like.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergstrom et al., J. Biol. Chem. 238, 3555 (1963) and Horton, Experienta 21, 113 (1965) and references cited therein. All of the so-called natural prostaglandins are derivatives of prostanoic acid:

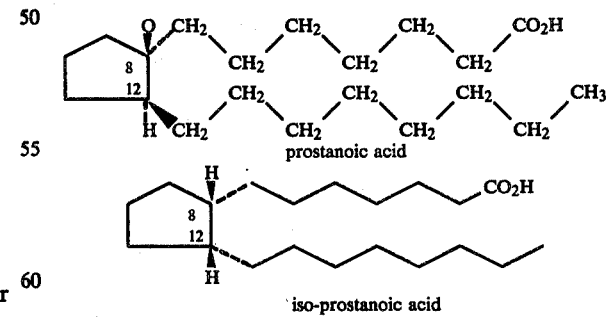

In iso-prostanoic acid the hydrogen atoms attached to C-8 and C-12 are in a cis configuration.

The natural prostaglandins have the prostanoic acid skeleton and they represent only one of the possible optical isomers. The compounds of the present invention include both those having the prostanoic acid structure and the iso-prostanoic acid structure as well as all of the possible optical isomers.

The novel compounds of the present invention may be readily prepared from certain substituted cyclopentenone intermediates (I) the preparation of which has already been described [U.S. Pat. No. 3,836,581; Netherlands Pat. No. 7310-276, Jan. 28, 1974 (Central Patents Index B-Farmdoc, 10735V/06); Netherlands Pat. No. 7310-277, Jan. 28, 1974 (Central Patents Index B-Farmdoc, 10736V/06)]and from certain substituted 1-mercapto-3-hydroxy compounds (II) as shown in Flowsheet A:

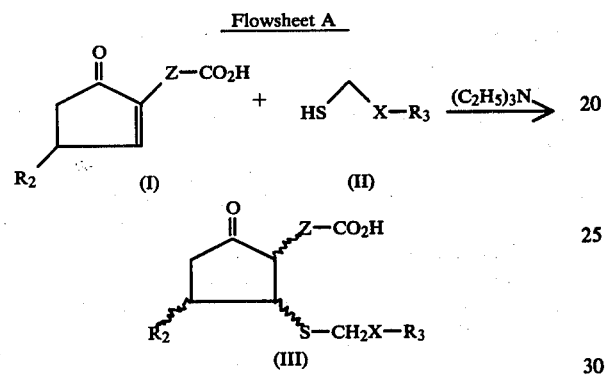

wherein $R_2$, Z, $R_3$ and X are as hereinabove defined. In general, the cyclopentenone (I) is mixed with 1 to 1.5 equivalents of the mercapto alcohol (II) and 1 to 1.2 equivalents of triethylamine, or other trialkylamine, in the absence of any solvent; an exothermic reaction usually ensues immediately. The reaction mixture is then allowed to stand at room temperature for 0.5 to 3.5 hours. The mixture is worked up by mixing with ether and dilute hydrochloric acid. From the ether layer one obtains the desired 13-thia prostanoic acids (III) as mixtures of isomers. The products of these reactions can be purified by various types of chromatography and if desired, the individual isomers can be isolated also by use of various chromatographic techniques well known to the art.

The preparation of the various 1-mercapto-3-hydroxy compounds used in this invention are outlined in Flowsheet B wherein $R_3$ and X are as hereinabove defined and the formula given by

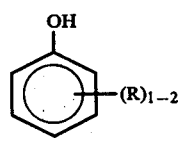

represents a phenol which is optionally substituted with one or two radicals selected from the group consisting of halogen trifluoromethyl, lower alkyl, and lower alkoxy radicals.

Flowsheet B

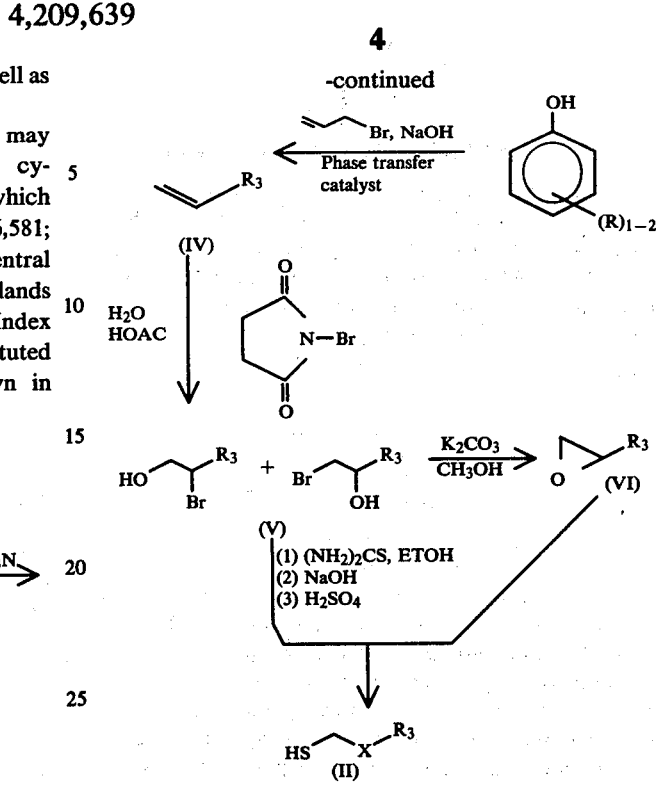

In those cases where $R_3$ is an alkyl group of 4 to 7 carbon atoms, the requisite olefins (IV) are commercially available. In those cases where $R_3$ is a substituted or unsubstituted phenoxymethyl group, the required olefin (IV) is prepared by reacting an appropriately substituted phenol with allyl bromide and sodium hydroxide in a two phase system consisting of water and benzene using a phase transfer catalyst $((C_8H_{17})_3 N^+CH_3Cl^-)$. The resulting olefins are then reacted with N-bromosuccinimide in water containing a small amount of acetic acid to give a mixture of bromohydrins (V). Depending on the nature of $R_3$, one can react the mixture of bromohydrins directly with thiourea in refluxing ethanol followed by sodium hydroxide and then neutralization with sulfuric acid to give the desired 1-mercapto-3-hydroxy compounds (II) or one can react the bromohydrins with potassium carbonate in methanol to give an epoxide (VI) which in turn is reacted with thiourea followed by sodium hydroxide; neutralization of the reaction mixture then gives the desired 1-mercapto-3-hydroxy compound (II) [F. G. Bordwell and H. M. Andersen, J. Amer. Chem. Soc., 75, 4959 (1953)].

Esters of the 13-thiaprostanoic acids of this invention may be prepared by reaction of the acids with the appropriate diazoalkane.

The 9-hydroxy derivatives of this invention (VII, 13-thiaprostaglandins of the F type) can be obtained as outlined in Flowsheet C wherein $R_2$, Z, $R_3$, and X are as hereinabove defined.

FLOWSHEET C

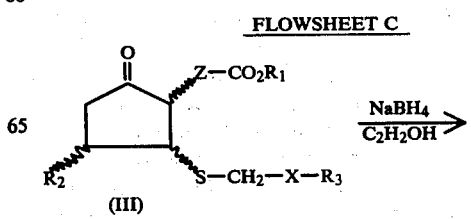

-continued

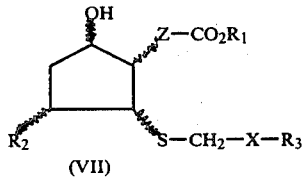
(VII)

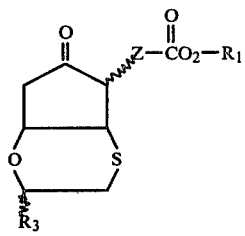

As Flowsheet C indicates, reduction of the 13-thiaprostanoic acids and esters (III) of this invention, either as isomeric mixtures or as separated isomers, with sodium borohydride in ethanol, according to procedures known to the art, readily gives the 9-hydroxy derivatives (VII) claimed in this invention. These 9-hydroxy derivatives are obtained as isomeric mixtures which can be separated, if desired, into component isomers by various chromatographic techniques well-known to the art.

The $\Delta^{10}$ derivatives included in this invention (IX, 13-thiaprostaglandins of the A type) are prepared by one of two methods outlined in Flowsheet D wherein Z, X, $R_1$ and $R_3$ are as hereinabove defined.

FLOWSHEET D

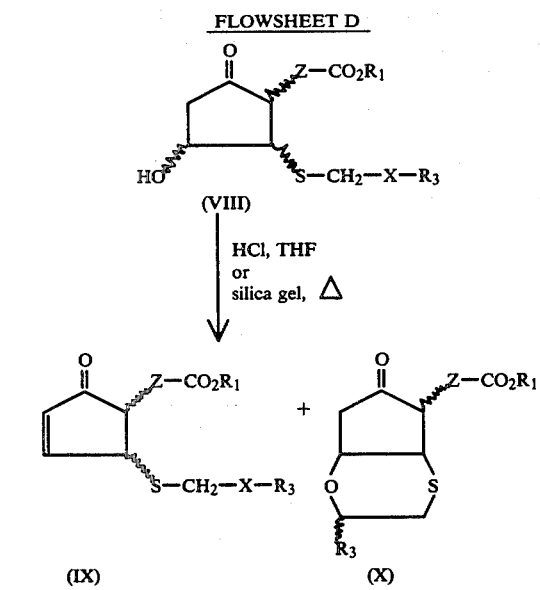

As shown in Flowsheet D, the reaction of the 13-thiaprostaglandins and their esters of the E type (VIII) either as mixtures of isomers or as the separated isomers using either dilute hydrochloric acid in tetrahydrofuran (THF) or by heating (VIII) after absorbtion on silica gel, gives the $\Delta^{10}$-13-thiaprostaglandins (IX) which are claimed in this invention as well as compounds with the general structure represented by (X). These latter type compounds (X) are formed by the addition of the 15-hydroxyl groups of (IX) to the $\Delta^{10}$ double bond. In cases wherein (VIII) is a mixture of isomers, the products (IX and X) are obtained as mixtures of isomers which, if desired, are separated into the individual component isomers by using various chromatographic techniques which are well known to the art.

Also embraced by the present invention are the novel compounds of the following general formula:

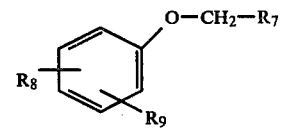

wherein Z, $R_1$ and $R_3$ are as hereinabove defined. For the preparation of these compounds see Flowsheet D above. The compounds of type (X) are useful in that they can be converted to the $\Delta^{10}$-13-thiaprostaglandins (IX) by treatment with acid.

The novel intermediate compounds of this invention are represented by the following formula are also embraced by this invention.

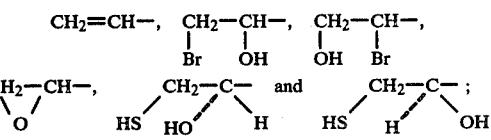

wherein $R_7$ is selected from the group consisting of $$CH_2=CH-,\ \ \underset{Br\ \ OH}{CH_2-CH-},\ \ \underset{OH\ \ Br}{CH_2-CH-},$$

$$\underset{O}{CH_2-CH-},\ \ \underset{HS\ \ HO}{CH_2-C-}\ \text{and}\ \underset{HS\ \ H}{CH_2-C-};$$

$R_8$ and $R_9$ are selected from the group consisting of halogen, lower alkyl of one to three carbon atoms, inclusive, lower alkoxy of one to three carbon atoms, inclusive, hydrogen and trifluoromethyl.

By using the procedure outlined in Flowsheet A, it is also possible to prepare individual enantiomers of III ($R_2$ is not hydrogen) by addition of the mercapto alcohols to the resolved 4-hydroxy-cyclopentenones (XI and XII) in which case III is obtained as a mixture of isomers each of which is optically active. The individual enantiomers can then be obtained by chromatographic procedures using, if necessary, multiple passes through a high pressure liquid chromatograph.

The 4-hydroxycyclopentenone racemates may be resolved into their component enantiomers (XI) and (XII) by derivatizing the ketone function with a reagent having an optically active center. The resulting diastereomeric mixture can then be separated by fractional crystallization, or by chromatography, or by high pressure liquid chromatography involving, if necessary, recycling techniques. Among the useful optically active ketone derivatizing reagents are 1-α-aminoxy-γ-methylpentanoic acid hydrochloride (to give XIII), (R)-2-aminoxy-3,3-dimethylbutyric acid hydrochloride, and 4α-methylbenzyl semicarbazide. After separation of the diastereomeric derivatives, reconstitution of the keto function provides the individual 4-hydroxycyclopentenone enantiomers (XI) and (XII). A useful procedure for the resolution of a 4-hydroxycyclopentenone racemate via an oxime such as (XIII) is described in the art [R. Pappo, P. Collins and C. Jung, *Tetrahedron Letters*, 943 (1973)].

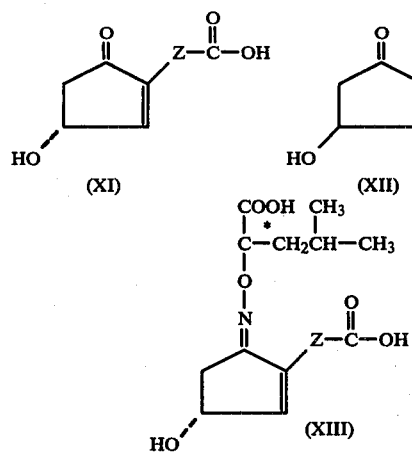

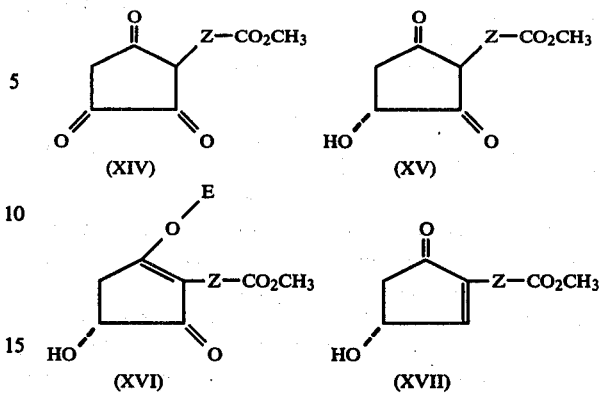

An alternative procedure for the preparation of the 4(R)-hydroxycyclopentenone enantiomers such as (XI) involves as a key step the selective microbiological or chemical reduction of trione (XIV) to the 4(R)-hydroxycyclopentanedione (XV). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis(o-anisylcyclohexylmethylphosphine)rhodium (I) tetrafluoroborate in the presence of one equivalent of organic base, such as triethylamine.

Conversion of hydrocyclopentanedione (XV) to an enol ether or enol ester, (XVI, E=alkyl, preferably isopropyl; aroyl such as benzoyl; or arylsulfonyl such as p-toluenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent a a temperature of about −10° to 15° C. Reduction of (XVI) with excess sodium bis(2-methoxyethoxy)aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (XVII). The ester (XVII) can be subjected to addition reactions as described hereinabove. The addition product will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C.J. Sih et al., *Journ. Amer. Chem. Soc.*, 95 1676 (1973); 97, 865 (1975); J.B. Heather et al., *Tetrahedron Letters*, 2213 (1973); R. Pappo and P. W. Collins, *Tetrahedron Letters*, 2627 (1972) and R. Pappo, P. Collins and C. Jung, *Ann. N.Y. Acad. Sci.*, 180, 64 (1971). For a descriptive of the baker's yeast procedure see C. J. Sih et al., *Journ. Amer. Chem. Soc.*, 94 3643 (1972); 97 857 (1975).

Procedures for the preparation of the requisite cyclopentanetriones (XIV) are well-established in the art and generally involve the treatment of an ω-1 oxo long chain ester (XVIII) with methyl or ethyl oxalate and a base such as sodium methoxide in methanol, followd by treatment with dilute hydrochloric acid in aqueous methanol to effect the dealkoxalylation of the intermediate (XIX). See J. Kutsube and M. Matsui, *Agr. Biol. Chem.*, 33, 1078 (1969); P. Collins, C. J. Jung and R. Pappo, *Israel Jounal of Chemistry*, 6, 839 (1968); R. Pappo, P. Collins and C. Jung, *Ann, N.Y. Acad. Sci.* 180, 64(1971); C. J. Sih et al., *Journ. Amer. Chem. Soc.*, 95, 1676 (1973) (see reference 7); and J. B. Heather et al., *Tetrahedron Letters*, 2313 (1973) for pertinent background literature.

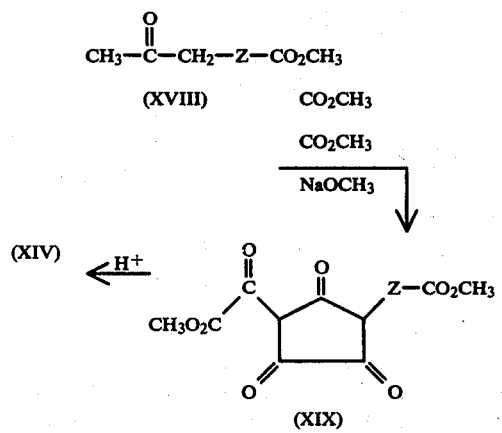

The intermediate keto ester (XVIII) may be prepared by a variety of methods known to the art. One useful procedure is outlined below and involves alkylation of ethyl acetoacetate sodium salt (XX) in the usual manner with the appropriate side-chain precursor (XXI X=Cl, Br, I, preferably Br or I) followed by decarbethoxylation and reesterification, all in the usual manner.

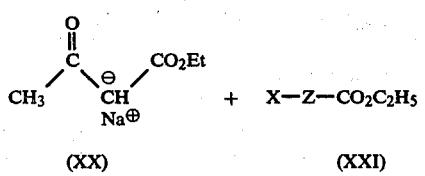

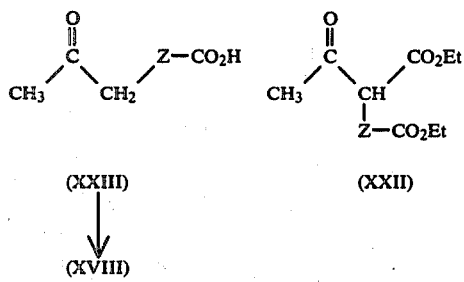

(XXIII)   (XXII)

↓

(XVIII)

The side-chain precursors (XXI) are commercially available where Z is —$(CH_2)_q$— and can be prepared as described in Belgian Pat. No. 786,215 (granted and opened to inspection Jan. 15, 1973) where Z is

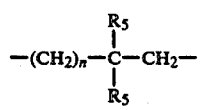

Where Z is

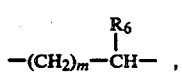

precursor (XXI) can be prepared as indicated below by mono-tetrahydropyranylation of the diol (XXIV) to (XXV), followed by mesylation, treatment of the resulting mesylate (XXVI) with appropriately substituted sodio malonate to give (XXVII), decarbethoxylation and reesterification to (XXVIII), mesylation of the second hydroxy function to (XXIX) and displacement with lithium bromide (or iodide) to (XXX). Alternatively, the ω-bromo alcohol (XXXI) after blocking as the tetrahydropyranyl derivative (XXXII), on treatment with the substituted sodio malonate provides (XXVII).

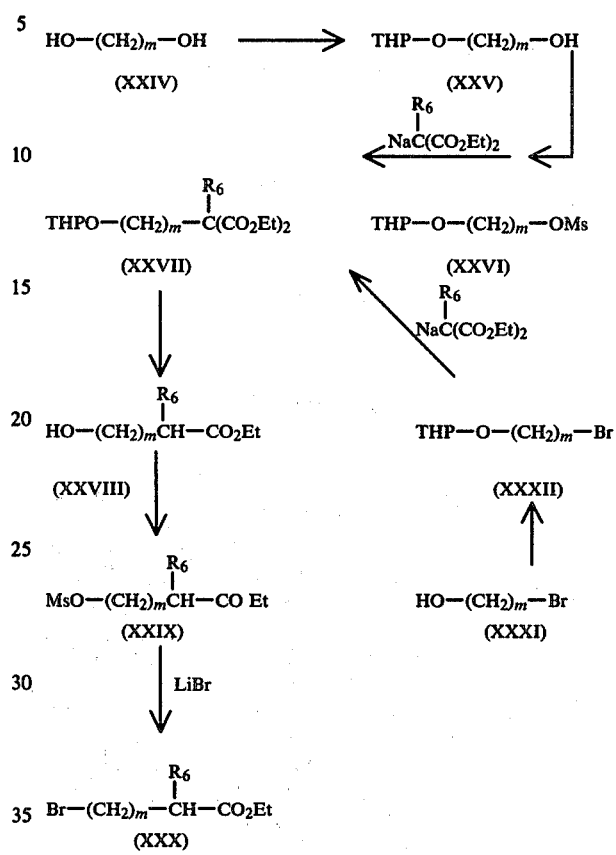

Those precursors wherein Z is —$(CH_2)_n$—O—$CH_2$— can be prepared by the transformation shown directly below starting with the mono-tetrahydropyranyl derivative (XXXIII). Thus, (XXXIII) is converted to the lithium alcoholate by treatment with butyl lithium, the alcoholate is then O-alkylated with ethyl bromoacetate to provide (XXXIV), which on de-tetrahydropyranylation, mesylation and reaction with lithium bromide gives the required (XXXVII). (These and all the above-described transformation can be effected in the usual manner, well-established in the art; pertinent examples for most of the reactions can be found in the above-cited Belgian Pat. No. 786,215.)

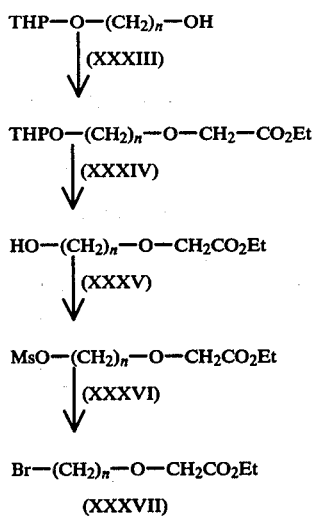

It is also possible to resolve the 4-hydroxycyclopentenone racemate (XXXVIII) by microbiological means. Thus, treatment of the 4-O-alkanoyl or aroyl derivatives (XXXIX), $R_{10}$=aryl or alkyl) of racemate (XXXVIII) (preferably the 4-O-acetyl and 4-O-propionyl derivatives) with an appropriate microorganism preferably a Saccharomyces species, e.g. (1375-143, affords preferential de-O-acylation of the 4(R)-enantiomer to give (XI), which is then separated from the unreacted 4(S)-O-acyl enantiomer (XL) by chromatographic procedures. After separation, mild hydrolysis of the 4(S) derivative (XL) provides the 4(S)-hydroxycyclopentenone (XII) [See N. J. Marsheck and M. Miyano, *Biochimica et Biophysica Acta*, 316, 363 (1973) for related examples.]

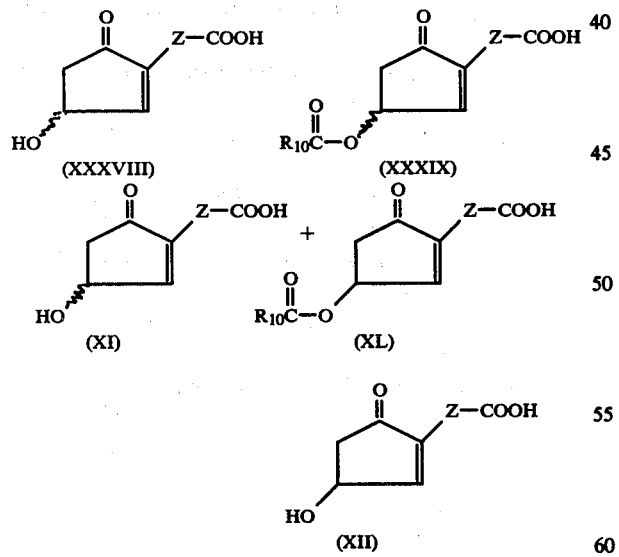

It is also possible to prepare the individual 4-hydroxycyclopentenones (XI) and (XII) directly be selective microbial hydroxylation of the corresponding 4-unsubstituted cyclopeteneone (XLI). For example, with *Aspergillus niger* ATTC 9142; a selective 4(R)-hydroxylation of (XLI, $Z=-(CH_2)_6-$) has been reported; for a literature example, see S. Kurozumi, T. Tora and S. Ishimoto, *Tetrahedron Letters*, 4959 (1973). Other organisms can also accomplish this hydroxylation.

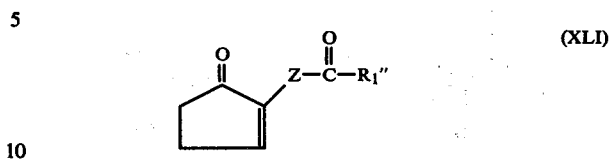

An alternate resolution procedure involves derivatization of the alcohol function of the racemic hydroxycyclopentenone to give ester-acid derivatives such as (XLII) wherein $R''_1$ is hydrogen or an alkoxy group, n' is zero or two and Z is as hereinabove defined.

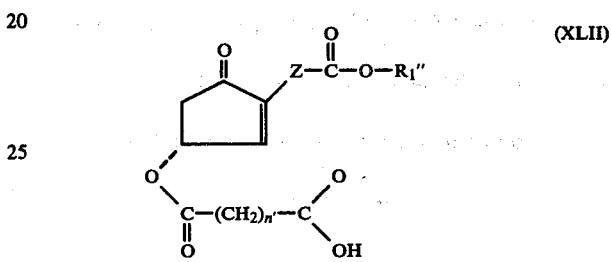

Such derivatives may be obtained from the corresponding free hydroxycyclopentenone by treatment in the usual manner with oxalyl chloride, succinyl chloride, succinic anhydride and the like. Treatment of the resulting acid or diacid ($R''_1$=hydrogen) with optically active amines e.g., 1-(-)-α-methylbenzylamine, d-(+)-α-methylbenzylamine, brucine, dehydroabietylamine, strychnine, quinine, cinchonine, qunidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(S)- and 4(R)-hydroxycyclopentenone enantiomers (XI) and (XII) or their respective esters. Cleavage of the oxalate acid ester (XLII, n=0) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); for an example of the use of succinate acid-ester see B. Goffinet, Ger. Offen. No. 2,263,880; *Chem. Abstracts*, 79, 78215z (1973).

By using the procedure outlined in Flowsheet A, it is also possible to prepare the individual enantiomers of (III) by the addition of the resolved 1-mercapto-2-hydroxy compounds (XLIII, R) and (XLIV, S) to the cyclopentenones (I) as shown below wherein Z, $R_2$ and $R_3$ are as hereinabove defined:

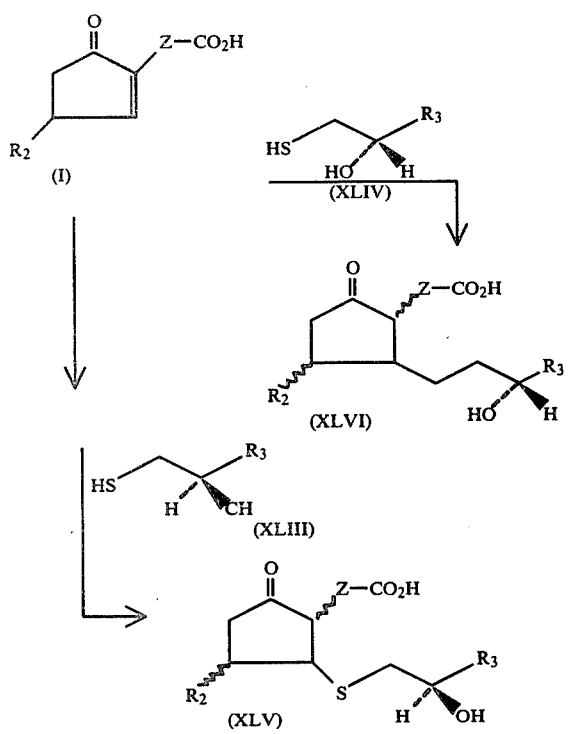

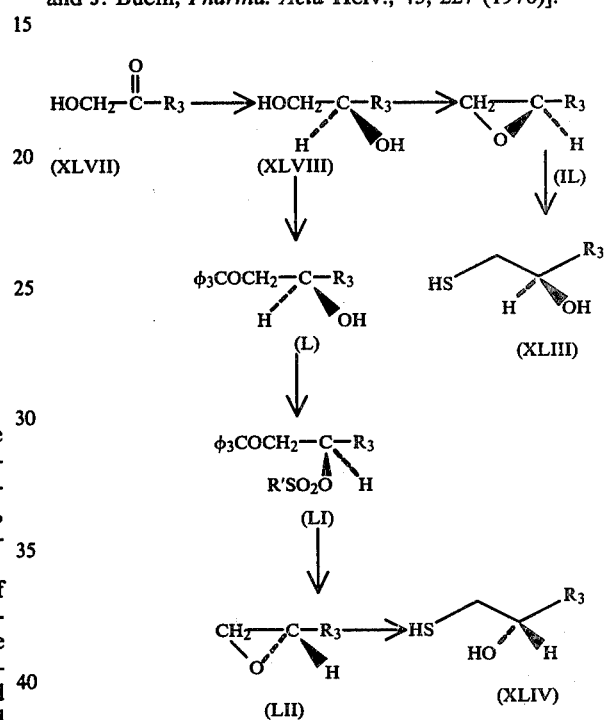

The resulting products (XLV) and (XLVI) will be obtained as a mixture of isomers each of which is optically active. The isomers can be separated by techniques well known to the art including, if necessary, multiple passes through a high pressure liquid chromatograph.

The resolved 1-mercapto-2-hydroxy compounds of the present invention (XLIII) and (XLIV) can be prepared as shown below wherein $R_3$ is as hereinabove defined. By use of a well-known and general microbiological reduction process, a 1-hydroxy-2-oxo compound (XLVII) is added to the fermenting mixture obtained from sucrose and baker's yeast (see P. A. Levene and A. Walt, Org. Synthesis, Coll. Col. II, p. 545 and N. Spassky, Bull. Soc. Chim. France, 1972, 4217, for appropriate examples). The reductase of this system stereospecifically provides the (R)-1,2-dihydroxy compounds (XLVIII). The glycol thus prepared is converted stereospecifically to the (R)-1,2-epoxide (IL) by one of several procedures known in the art (see B. T. Golding et al., Journ. Chim. Soc. Perkin I, 1973, 1214 and M. S. Newman and C. M. Chen, Journ. Amer. Chem. Soc., 95, 278 (1973), for appropriate examples). The stereospecific conversion of this epoxide to the (R)-1-mercapto-2-hydroxy compound (XLIII) may be accomplished by the reaction of this epoxide with thiourea as described hereinabove.

The (R)-1,2-dihydroxy compound (XLVIII) obtained from the yeast fermentation may also be used for the preparation of the (S)-1-mercapto-2-hydroxy compounds (XLIV). Preferential triphenylmethylation of the primary alcohol group provides the monoether (L) (see L. J. Stegerhoek and P. E. Verkade, Rec. Trav. Chim. 74, 143 (1955) for pertinent literature). The remaining alcohol group is esterified with a sulfonyl halide such p-toluenesulfonyl chloride to provide the sulfonate ester (LI). Catalytic hydrogenolysis of the trityl group followed by treatment of the resulting free primary alcohol with a strong base, e.g. potassium hydroxide in methyl alcohol, provides the epoxide of the opposite configuration, a (S)-1,2-epoxide (LII) (see J. Fried, et al. Journ. Amer. Chem. Soc., 94, 4343 (1972) and J. W. Cornforth et al. Journ. Chem. Soc., 1959, 112, for pertinent literature). This substance is reacted with thiourea as described hereinabove to provide the (s)-1-mercapto-2-hydroxy compound (XLIV).

The starting 1-hydroxy-2-oxo compounds for this procedure may be prepared in a variety of ways well-known to the literature [see P. A. Levene and M. L. Maller, Journ. Biol. Chem. 79, 475 (1928) and I. Forgo and J. Buchi, Pharma. Acta Helv., 45, 227 (1970)].

With reference to the configuration of substituents on the five-membered ring of the compounds described in this invention, the terms α and β refer to substituents which are below and above the plane of the paper, respectively; for example, in the structure shown below $R_1$ and $R_3$ have an α configuration and $R_2$ has a β configuration.

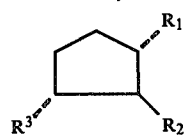

Certain characteristics of the five-membered ring of the novel compounds of this invention allow them to be classified as follows:

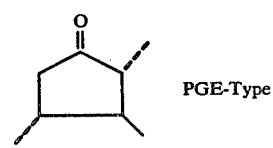

PGE-Type

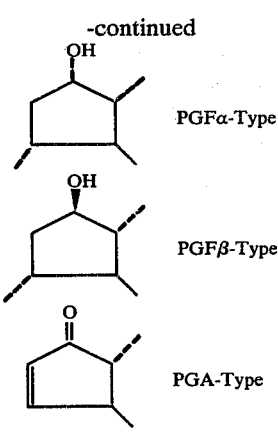

PGFα-Type

PGFβ-Type

PGA-Type

The novel compounds of this invention possess the pharmacological activity described below as associated with the appropriate above described prostaglandin type.

The known PGE, PGFα, PGFβ and PGA compounds are all potent in causing multiple biological responses even at low doses. For example, PGE$_1$ and PGE$_2$ are extremely potent in causing vasodepression and smooth muscle stimulation and also are potent as antilipolytic agents. Thus, for many applications, these known prostaglandins lack selectivity of biological activity. In contrast, the novel prostaglandin analogs of this invention are more specific with regard to potency in causing prostaglandin-like biological responses. Therefore, each of these novel prostaglandin analogs is surprisingly and unexpectedly more useful than one of the corresponding above-mentioned known prostaglandins for at least one of the pharmacological purposes indicated below for the latter, because it has a different and narrower spectrum of biological activity than the known prostaglandins, and therefore is more specific in its activity and causes smaller and fewer undesired side effects than the known prostaglandins.

Another advantage of the novel compounds of this invention, compared with the known prostaglandins, is that these novel compounds are administered effectively orally, sublingueally, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter or smaller doses, and make possible self-administration by the patient.

PGE$_1$, PGE$_2$, and the corresponding PGFα, PGFβ, and PGA, compounds, and their esters and pharmacologically acceptable salts, are extremely potent in causing various biological responses. For that reason, these compounds are useful for pharmacological purposes. See, for example, Bergstrom et al., Pharmacol. Rev. 20, 1(1968), and references cited therein. A few of those biological responses are systemic arterial blood pressure lowering in the case of the PGE$_2$, PGFβ and PGA compounds as measured, for example, in anesthetized (penobarbital sodium) pentolinium-treated rats with indwelling aortic and right heart cannulas; pressor activity, similarly measured, for the PGFα compounds; stimulation of smooth muscle as shown, for example, by tests on strips of guinea pig ileum, rabbit duodenum, or gerbil colon: potentiation of other smooth muscle stimulants; antiipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion: activity on the central nervous system; decrease of blood platelet adhesiveness in the case of PGE compounds as shown by platelet-to glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration. These compounds may also be useful in conjunction with various non-steroidal anti-inflammatory agents such as aspirin, phenylbutazone, indomethacin, and the like to minimize the well known ulcerogenic effects of the latter.

The PGF compounds are useful when ever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg. per kg. of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g., oxytocic agents, e.g., oxytocin, and the various ergot alkaloids including derivatives and analogs thereof. Therefore PGE$_2$, for example, is useful in place of or in combination with less than usual amounts of these known smooth muscle stimulators, for example, to relieve the symptoms or paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous subcutaneous or intramuscular injection or infusion during puerperium in the range of 0.01 to 2 mg. per kg. of body weight per day, the exact dose depending on the age, weight, and condition of the patient or animal.

The PGE, PGFβ and PGA compounds are useful as hypotensive agents to reduce blood pressure in mammals including man. For this purpose, the compounds are administered by intravenous infusion at the rate about 0.01 to about 50 μg. per kg. of body weight per minute, or in a single or multiple dose of about 25 to 2500 μg. per kg. of body weight total per day.

The PGE, PGFα, and PGFβ compounds are useful in place of oxytocin to induce labor in pregnant female animals, including man, cows, sheep, pigs, at our near term or in pregnant animals with intrauterine death of the fetus from about 20 weeks to term. For this purpose, the compound is infused intravenously at a dose 0.01 to 50 μg. per kg. of body weight per minute until or near the termination of the second stage of labor, i.e., expulsion of the fetus. These compounds are especially useful when the female is one or more weeks postmature and natural labor has not started, or 12 to 60 hours after the membrane have ruptured and natural labor has not yet started.

The PGE, PGFα, and PGFβ compounds are useful for controlling the reproductive cycle in ovulating female mammals, including humans and other animals. For that purpose, PGF$_{2α}$, for example, is administered systematically at a dose level in the range 0.01 mg. to about 20 mg. per kg. of body weight, advantageously during a span of time starting approximately at the time of ovulation and ending approximately at the time of menses or just prior to menses. Additionally, expulsion of an embryo or fetus is accomplished by similar administration of the compound during the first third or second third of the normal mammalian gestation period. Accordingly, they are useful as abortifacients. They are also useful for induction of menses during approximately the first two weeks of a missed period and accordingly are useful as contraceptive anti-fertility agents.

The PGA compounds are derivatives and salts thereof increase the flow of blood in the mammalian kidney, there by increasing volume and electrolyte content of the urine. For that reason, PGA compounds are useful in managin cases of renal disfunction, especially in cases of several impaired renal blood flow, for example, the hepatorena syndrome and early kidney transplant rejection. In case of excessive or inappropriate ADH (antidiuretic hormone vasopressin) secretion, the diuretic effect of these compounds is even greater. In anephretic states, the vasopressin action of these compounds is especially useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticord steroids, for example, hydrocortizone, prednisolone, methylprednisolone, and fluprednisolone, each of those being used in the combination at the usual concentration suitable for its use alone.

The novel compounds of this invention induce the biological responses described hereinabove as associated with its particular prostaglandin type. These novel compounds are accordingly useful for the above-described corresponding purposes, and may be used for those purposes in the same manner as described above.

The novel PGE, PGFβ and PGA compounds of this invention are also useful as bronchodilators for the treatment of asthma and chronic bronchitis; as such they may be conveniently administered by inhalation of aerosol sprays prepated in a dose range of about 10 μg. to about 10 mg. per ml. of ap pharmacologically suitable liquid vehicle.

In addition certain of the novel compounds of this invention are useful for the preparation of other novel compounds of this invention.

A preferred embodiment of this invention may be represented by the following formula:

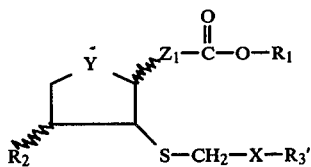

wherein $R_1$, $R_2$, Y and X are as hereinabove defined and $Z_1$ is a divalent radical selected from the group consisting of those of the formulae:

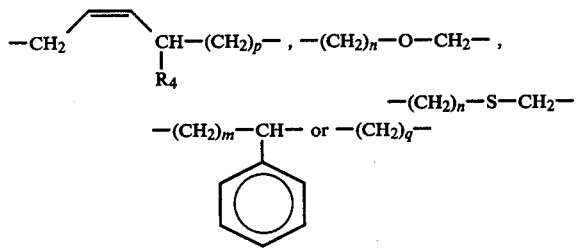

wherein $R_4$, p, q, n and m are as hereinabove defined; $R'_3$ is selected from the group consisting of a phenoxymethyl group in which the phenyl ring is optionally substituted with one or two radicals selected from the group consisting of halogen, trifluoromethyl, alkyl having up to 3 carbon atoms, and alkoxy having up to 3 carbon atoms; and wherein the moiety of the formula:

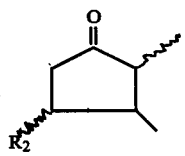

may be the moiety of the formula:

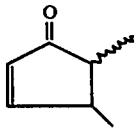

This application will be described in greater detail in conjunction with the following specific examples.

EXAMPLE 1

Preparation of 3-(4-fluorophenoxy)propene

To a solution of 125 g. (1.12 mol) of 4-fluorophenol (Aldrich Chemical Co.) in 300 ml. of water containing 56.0 g. (1.4 mol) of sodium hydroxide is added a solution of 211.5 g. (1.75 mol) of allyl bromide and 5.0 g. of methyl tricaprylyl ammonium chloride in 150 ml. of benzenes. The mixture is stirred vigorously. After 15 minutes the reaction mixture begins to exotherm and is cooled in an ice bath for 15 minutes after which the solution is stirred at room temperature for 24 hours. The reaction mixture is diluted with water and extracted several times with ether. The ether solution is washed twice with water, once with dilute sodium hydroxide and once with saturated sodium chloride solution. The solution is then dried with magnesium sulfate, treated with Norite, and filtered through a pad of silica gel. The ether is removed and the residue is distilled (46°–50° C., 0.2 mm) to give 139.0 g. (0.91 mol) of 3-(4-fluorophenoxy)propene.

NMR: $\delta_{ms}^{CDCl_3}$, 7.10–6.76 (m, 4H, aromatic), 6.23–5.86 (m, 1H, vinyl), 5.55–5.22 (m, 2H, vinyl), 4.52 (m, 2H, CH$_2$). IR: neat, 1600, 1502, 1210, 827, 767 cm$^{-1}$.

EXAMPLE 2–10

By the procedure described in Example 1, the various 3-phenoxypropenes listed in Table I are prepared.

TABLE I

| Example | Starting Phenol | Product |
|---|---|---|
| 2 | 3-trifluoromethylphenol | 3(3-trifluoromethylphenoxy)propene |
| 3 | 3-chlorophenol | 3(3-chlorophenoxy)propene |
| 4 | 2-methylphenol | 3(2-methylphenoxy)propene |
| 5 | 3-methoxyphenol | 3(3-methoxyphenoxy)propene |
| 6 | 3,4-dichlorophenol | 3(3,4-dichlorophenoxy)propene |
| 7 | 3-fluorophenol | 3(3-fluorophenoxy)propene |
| 8 | 4-chlorophenol | 3(4-chlorophenoxy)propene |
| 9 | 2-chloro-4-methylphenol | 3(2-chloro-4-methylphenoxy)propene |
| 10 | 4-bromophenol | 3(4-bromophenoxy)propene |

EXAMPLE 11

Preparation of 1-hydroxy-2-bromo-3-(4-fluorophenoxy)propane and 1-bromo-2-hydroxy-3-(4-fluorophenoxy)propane A mixture of 120.0 g. (0.799 mol) of 3-(4-fluorophenoxy)propene, 163.6 g. (0.92 mol) of n-bromosuccinimide, and 1.5 ml. of acetic acid in 1250 ml. of water is stirred vigorously for 4 days at room temperature. The aqueous layer is decanted from an orange oil. The aqueous layer is extracted with ether. The ether solution is combined with the oil and the resulting solution is washed twice with water, once with a saturated solution of sodium bicarbonate, once with a 5% solution of sodium thiosulfate, and once with a saturated solution of sodium chloride. The solution is dried over magnesium sulfate and treated with Norite. The solvent is removed and the residue is distilled to give 168 g. (85% of a mixture of 1-hydroxy-2-bromo-3-(4-fluorophenoxy)propane and 1-bromo-2-hydroxy-3-(4-fluorophenoxy)propane (116°–119° C., 0.1mm).

IR: neat, 3440, 1601, 1515, 1460, 830, 763 cm$^{-1}$.

EXAMPLES 12–22

By the procedure described in Example 11, the various 1-hydroxy-2-bromo and 1-bromo-2-hydroxy compounds listed in Tables II and III are prepared.

TABLE II

| Example | Starting olefin of Example | Products |
|---|---|---|
| 12 | 2 | 1-hydroxy-2-bromo-3-(3-trifluoromethylphenoxy)propane and 1-bromo-2-hydroxy-3-(3-trifluoromethylphenoxy)propane |
| 13 | 3 | 1-hydroxy-2-bromo-3-(3-chlorophenoxy)propane and 1-bromo-2-hydroxy-3-(3-chlorophenoxy)propane |

TABLE II-continued

| Example | Starting olefin of Example | Products |
|---|---|---|
| 14 | 4 | 1-hydroxy-2-bromo-3-(2-methylphenoxy)propane and 1-bromo-2-hydroxy-3-(2-methylphenoxy)propane |
| 15 | 5 | 1-hydroxy-2-bromo-3-(3-methoxyphenoxy)propane and 1-bromo-2-hydroxy-3-(3-methoxyphenoxy)propane |
| 16 | 6 | 1-hydroxy-2-bromo-3-(3,4-dichlorophenoxy)propane and 1-bromo-2-hydroxy-3-(3,4-dichlorophenoxy)propane |
| 17 | 7 | 1-hydroxy-2-bromo-3-(3-fluorophenoxy)propane and 1-bromo-2-hydroxy-3-(3-fluorophenoxy)propane |
| 18 | 8 | 1-hydroxy-2-bromo-3-(4-chlorophenoxy)propane and 1-bromo-2-hydroxy-3-(4-chlorophenoxy)propane |
| 19 | 9 | 1-hydroxy-2-bromo-3-(2-chloro-4-methylphenoxy)propane and 1-bromo-2-hydroxy-3-(2-chloro-4-methylphenoxy)propane |
| 20 | 10 | 1-hydroxy-2-bromo-3-(4-bromophenoxy)propane and 1-bromo-2-hydroxy-3-(4-bromophenoxy)propane |

TABLE III

| Example | Starting olefin | Products |
|---|---|---|
| 21 | 1-hexene | 1-hydroxy-2-bromohexane and 1-bromo-2-hydroxyhexane |
| 22 | 1-octene | 1-hydroxy-2-bromooctane and 1-bromo-2-hydroxyoctane |

EXAMPLE 23

Preparation of 1,2-epoxy-3-(4-fluorophenoxy)propane

To a solution of 104 g. (0.42 mol.) of the mixture of 1-bromo-2-hydroxy-3-(4-fluorophenoxy)propane and 1-hydroxy-2-bromo-3-(4-fluorophenoxy)propane in 480 ml. of methanol is added a solution of 74 g. (0.53 mol) of potassium carbonate in 250 ml. of water. The mixture is stirred at room temperature for 23 hours. Most of the methanol is removed at reduced pressure and the residue is poured in water. The mixture is extracted with ether. The ether solution is washed with a saturation solution of sodium chloride and dried over magnesium sulfate. The solvent is removed to give 71.3 g. (100%) of 1,2-epoxy-3-(4-fluorophenoxy)propane. p IR: neat, 3100, 3030, 2970, 2900, 1601, 1515, 1461, 1215, 1040, 830, 776, 750 cm$^{-1}$.

EXAMPLES 24–32

By the procedure described in Example 23, the various 1,2-epoxy-3-phenoxypropanes listed in Table IV are prepared.

TABLE IV

| Example | 1-Hydroxy-2-bromo-2-hydroxy-3-phenoxy propanes of Example | Product |
|---|---|---|
| 24 | 12 | 1,2-epoxy-3-(3-trifluoromethylphenoxy)propane |
| 25 | 13 | 1,2-epoxy-3-(3-chlorophenoxy)propane |
| 26 | 14 | 1,2-epoxy-3-(2-methylphenoxy)propane |
| 27 | 15 | 1,2-epoxy-3-(3-methoxyphenoxy)propane |
| 28 | 16 | 1,2-epoxy-3-(3,4-dichlorophenoxy)propane |
| 29 | 17 | 1,2-epoxy-3-(3-fluorophenoxy)propane |
| 30 | 18 | 1,2-epoxy-3-(4-chlorophenoxy)propane |
| 31 | 19 | 1,2-epoxy-3-(2-chloro-4-methylphenoxy)propane |
| 32 | 20 | 1,2-epoxy-3-(4-bromophenoxy)propane |

EXAMPLE 33

Preparation of 1-mercapto-2-hydroxy-3-(4-fluorophenoxy) propane

A mixture of 38.0 g. (0.499 mol) of thiourea and 14 ml. of sulfuric acid is stirred at 0° C. in 380 ml. of tetrahydrofuran as a solution of 70.8 g. (0.421 mol.) of 1,2-epoxy-3-(4-fluorophenoxy) propane in 200 ml. of tetrahydrofuran is added dropwise over a 20 minute period. The mixture is then stirred an additional 0.5 hour. at 0° C. and 0.75 hour at room temperature. Most of the solvent is removed at reduced pressure and the residue is mixed with ether. The mixture is then filtered and a white solid is collected which is then washed twice with ether. The resulting solid is added portionwise to a stirred solution of 72 g. of sodium hydroxide in 300 ml. of water. After stirring 1 hour the solution is washed with ether. The aqueous solution is poured into a cold solution of 143 ml. of sulfuric acid in 400 ml. of water. The mixture is extracted with ether. The ether solution is washed with dilute sodium bicarbonate solution, saturated sodium chloride solution and dried over magnesium sulfate. The solvent is removed and the residue is distilled (134°–138° 0.05 mm) to give 40.2 g. of 1-mercapto-2-hydroxy-3-(4-fluorophenoxy)propane.

NMR: $\delta_{TMS}^{CDCl_3}$, 6.93 (m, 4H, aromatic), 4.02 (m, 3H, α to oxygen), 3.10 (s, 1H, OH), 2.80 (m, 2H, CH$_2$S), 1.58 (t, 1H, SH, J=8.6Hz).

EXAMPLES 34–42

By the procedure described in example 33, the various 1-mercapto-2-hydroxy-3-phenoxypropanes listed in Table V are prepared.

TABLE V

| Example | 1,2-epoxy-3-phenoxy propane of Example | Product |
|---|---|---|
| 34 | 24 | 1-mercapto-2-hydroxy-3-(3-trifluoromethylphenoxy)propane |
| 35 | 25 | 1-mercapto-2-hydroxy-3-(3-chlorophenoxy)propane |
| 36 | 26 | 1-mercapto-2-hydroxy- |

TABLE V-continued

| Example | 1,2-epoxy-3-phenoxy propane of Example | Product |
|---|---|---|
| | | 3-(2-methylphenoxy)-propane |
| 37 | 27 | 1-mercapto-2-hydroxy-3-(3-methoxyphenoxy)-propane |
| 38 | 28 | 1-mercapto-2-hydroxy-3-(3,4-dichlorophenoxy)propane |
| 39 | 29 | 1-mercapto-2-hydroxy-3-(3-fluorophenoxy)-propane |
| 40 | 30 | 1-mercapto-2-hydroxy-3-(4-chlorophenoxy)-propane |
| 41 | 31 | 1-mercapto-2-hydroxy-3-(2-chloro-4-methylphenoxy)propane |
| 42 | 32 | 1-mercapto-2-hydroxy-3-(4-bromophenoxy)propane |

EXAMPLE 43

Preparation of 1-mercapto-2-hydroxyheptane

To a mixture of 50.0 g. (0.256 mol) of 1-bromo-2-hydroxyheptane and 1-hydroxy-2-bromoheptane [I. Forgo and J. Buchi, *Pharm. Acta Helv.*, 45, 231 (1970)] is added 80 ml. of ethanol and 30.0 g. (0.39 mol) of thiourea. The mixture is stirred at 90°–100° C. for 1.5 hour. The ethanol is removed at reduced pressure. The residue is stirred with ether (400 ml.) for 1 hour. The mixture is filtered and a white solid is collected which is washed several times with more ether. This solid is dissolved in 200 ml. of water. The resulting solution is added dropwise to a solution of 31.2 g. (0.78 mol) of sodium hydroxide in 100 ml. of water over a 25 minute period. After stirring an additional 20 minutes the solution is poured into a cold solution of 76 g. of sulfuric acid in 275 ml. of water. The mixture is extracted with ether and the ether solution is washed with a saturated solution of sodium bicarbonate and a saturated solution of sodium chloride. The ether solution is dried over magnesium sulfate. The solvent is removed and the residue is distilled (56°–57° C. 0.5 mm) to give 19.6 g. of 1-mercapto-2-hydroxyheptane NMR: $\delta_{TMS}^{CDCl_3}$, 3.61 (m, 1H, C$\underline{H}$OH), 2.62 (m, 3H, CH$_2$S, OH) 1.42 (m, 9H, methylenes, 5H), 0.90 (m, 3H, terminal methyl) IR: neat, 3380 (OH), 2560 (SH) cm$^{-1}$.

EXAMPLES 44–45

By the procedure described in Example 43, the various 1-mercapto-2-hydroxy alkanes listed in Table VI are prepared.

TABLE VI

| Example | Starting 1-hydroxy-2-bromo and 1-bromo-2-hydroxy alkanes of Example | Product |
|---|---|---|
| 44 | 21 | 1-mercapto-2-hydroxy-hexane |
| 45 | 22 | 1-mercapto-2-hydroxy-octane |

EXAMPLE 46

Preparation of 2-(6-methyl-6-carboxyhexyl)-3-(2-hydroxyheptylthio)cyclopentanone To 2.0 g. (0.0089 mol) of 2-(6-methyl-6-carboxyhexyl)-cyclopent-2-en-1-one is added 1.68 g. (0.0113 mol) of 1-mercapto-2-hydroxy heptane and 0.9 g. (0.0089 mol) or triethylamine. The reagents are mixed as a mild exothermic reaction ensues. After standing 3.5 hours at room temperature, the resulting oil is washed several times with hexane and then mixed with ether and dilute hydrochloric acid. The ether layer is washed with a saturated solution of sodium chloride and dried over magnesium sulfate. The ether is removed giving 3.38 g. of an oil which is purified by partition chromatography on Celite using a mixture of heptane, methylene chloride, methanol, and water in a ratio of 85:15:15:6 as the mobile phase to give 1.75 g. (0.0047 mol) of 2-(6-methyl-6-carboxyhexyl)-3-(2-hydroxyheptylthio)cyclopentanone NMR: $\delta_{TMS}^{CDCl_3}$, 6.15 (bs, 2H, OH), 3.68 (m, 1H, $\alpha$ to OH), 3.23–2.90 (m, 9H, protons $\alpha$ to sulfur and carbonyl, cyclopentanone methylene), 1.34 (m, 18H, methylenes), 1.17 ($\alpha$, 3H, CHCH$_3$, J=6.6Ht), 0.90 (m, 3H, terminal methyl).

MS: m/e, 354 (m—H$_2$O).

EXAMPLES 47–104

By the procedure described in Example 46, the various cyclopentanones listed in Table VII are prepared.

TABLE VII

| Example | 1-mercapto-2-hydroxy compound of Example | Starting cyclopentenone | Product |
|---|---|---|---|
| 47 | 33 | 2-(6-methyl-6-carboxyhexyl)cyclopent-2-en-1-one | 2-(6-methyl-6-carboxyhexyl)-3-[2-hydroxy-3-(4-fluorophenoxy)propylthio]cyclopentanone |
| 48 | 34 | 2-(6-methyl-6-carboxyhexyl)-cyclopent-2-en-1-one | 2-(6-methyl-6-carboxyhexyl)-3-[2-hydroxy-3-(3-trifluoromethylphenoxy)propylthio]-cyclopentanone |
| 49 | 35 | 2-(6-methyl-6-carboxyhexyl)-cyclopent-2-en-1-one | 2-(6-methyl-6-carboxyhexyl)-3-[2-hydroxy-3-(3-chlorophenoxy)propylthio]cyclopentanone |
| 50 | 36 | 2-(6-methyl-6-carboxyhexyl)-cyclopent-2-en-1-one | 2-(6-methyl-6-carboxyhexyl)-3-[2-hydroxy-3-(2-methylphenoxy)propylthio]cyclopentanone |
| 51 | 44 | 2-(6-methyl-6-carboxyhexyl)-cyclopent-2-en-1-one | 2-(6-methyl-6-carboxyhexyl)-3-(2-hydroxy-hexylthio)cyclopentanone |
| 52 | 33 | 2-(6-ethyl-6-carboxyhexyl)-cyclopent-2-en-1-one | 2-(6-ethyl-6-carboxyhexyl)-3-[2-hydroxy-3-(4-fluorophenoxy)propylthio]cyclopentanone |

TABLE VII-continued

| Example | 1-mercapto-2-hydroxy compound of Example | Starting cyclopentenone | Product |
|---|---|---|---|
| 53 | 34 | 2-(6-ethyl-6-carboxyhexyl)-cyclopent-2-en-1-one | 2-(6-ethyl-6-carboxyhexyl)-3-[2-hydroxy-3-(3-trifluoromethylphenoxy)propylthio]-cyclopentenone |
| 54 | 35 | 2-(6-ethyl-6-carboxyhexyl)-cyclopent-2-en-1-one | 2-(6-ethyl-6-carboxyhexyl)-3-[2-hydroxy-3-chlorophenoxy)propylthio]cyclopentanone |
| 55 | 37 | 2-(6-ethyl-6-carboxyhexyl)-cyclopent-2-en-1-one | 2-(6-ethyl-6-carboxyhexyl)-3-[2-hydroxy-3-(3-methoxyphenoxy)propylthio]cyclopentanone |
| 56 | 45 | 2-(6-ethyl-6-carboxyhexyl)-cyclopent-2-en-1-one | 2-(6-ethyl-6-carboxyhexyl)-3-(2-hydroxy-octylthio)cyclopentanone |
| 57 | 43 | 2-(6-ethyl-6-carboxyhexyl)-cyclopent-2-en-1-one | 2-(6-ethyl-6-carboxyhexyl)-3-(2-hydroxy-heptylthio)cyclopentanone |
| 58 | 33 | 2-(6-phenyl-6-carboxyhexyl)-cyclopent-2-en-1-one | 2-(6-phenyl-6-carboxyhexyl)-3-[ 2-hydroxy-3-(4-fluorophenoxy)propylthio]cyclopentanone |
| 59 | 34 | 2-(6-phenyl-6-carboxyhexyl)-cyclopent-2-en-1-one | 2-(6-phenyl-6-carboxyhexyl)-3-[2-hydroxy-3-(3-trifluoromethylphenoxy)propylthio]-cyclopentanone |
| 60 | 35 | 2-(6-phenyl-6-carboxyhexyl)-cyclopent-2-en-1-one | 2-(6-phenyl-6-carboxyhexyl)-3-[2-hydroxy-3-(3-chlorophenoxy)propylthio]cyclo-pentanone |
| 61 | 38 | 2-(6-phenyl-6-carboxyhexyl)-cyclopent-2-en-1-one | 2-(6-phenyl-6-carboxyhexyl)-3-[2-hydroxy-3-(3,4-dichlorophenoxy)propylthio]-cyclopentanone |
| 62 | 43 | 2-(6-phenyl-6-carboxyhexyl)-cyclopent-2-en-1-one | 2-(6-phenyl-6-carboxyhexyl)-3-(2-hydroxy-heptylthio)cyclopentanone |
| 63 | 44 | 2-(6-phenyl-6-carboxyhexyl)-cyclopent-2-en-1-one | 2-(6-phenyl-6-carboxyhexyl)-3-(2-hydroxy-hexylthio)cyclopentanone |
| 64 | 33 | 2-(6-carboxyhexyl)cyclopent-2-en-1-one | 2-(6-carboxyhexyl)-3-[2-hydroxy-3-(4-fluorophenoxy)propylthio]cyclopentanone |
| 65 | 34 | 2-(6-carboxyhexyl)cyclopent-2-en-1-one | 2-(6-carboxyhexyl)-2-[2-hydroxy-3-(3-trifluoromethylphenoxy)propylthio]cyclo-pentanone |
| 66 | 35 | 2-(6-carboxyhexyl)cyclopent-2-en-1-one | 2-(6-carboxyhexyl)-3-[2-hydroxy-3-(3-chlorophenoxy)propylthio]cyclopentanone |
| 67 | 39 | 2-(6-carboxyhexyl)cyclopent-2-en-1-one | 2-(6-carboxyhexyl)-3-[2-hydroxy-3-(3-fluorophenoxy)propylthio]cyclopentanone |
| 68 | 40 | 2-(6-carboxyhexyl)cyclopent-2-en-1-one | 2-(6-carboxyhexyl)-3-[2-hydroxy-3-(4-chlorophenoxy)propylthio]cyclopentanone |
| 69 | 33 | 2-(5,5-dimethyl-6-carboxy-hexyl)cyclopent-2-en-1-one | 2-(5,5-dimethyl-6-carboxyhexyl)-3-[2-hydroxy-3-(4-fluorophenoxy)propylthio]-cyclopentanone |
| 70 | 34 | 2-(5,5-dimethyl-6-carboxy-hexyl)cyclopent-2-en-1-one | 2-(5,5-dimethyl-6-carboxyhexyl)-3-[2-hydroxy-3-(3-trifluoromethylphenoxy)-propylthio]cyclopentanone |
| 71 | 35 | 2-(5,5-dimethyl-6-carboxy-hexyl)cyclopent-2-en-1-one | 2-(5,5-dimethyl-6-carboxyhexyl)-3-[2-hydroxy-3-(3-chlorophenoxy)propylthio]-cyclopentanone |
| 72 | 41 | 2-(5,5-dimethyl-6-carboxy-hexyl)cyclopent-2-en-1-one | 2-(5,5-dimethyl-6-carboxyhexyl)-3-[2-hydroxy-3-(2-chloro-4-methylphenoxy)-propylthio]cyclopentanone |
| 73 | 43 | 2-(5,5-dimethyl-6-carboxy-hexyl)cyclopent-2-en-1-one | 2-(5,5-dimethyl-6-carboxyhexyl)-3-(2-hydroxyheptylthio)cyclopentanone |
| 74 | 45 | 2-(5,5-dimethyl-6-carboxy-hexyl)cyclopent-2-en-1-one | 2-(5,5-dimethyl-6-carboxyhexyl)-3-(2-hydroxyoctylthio)cyclopentanone |
| 75 | 33 | 2-(6-carboxy-5-oxahexyl)-cyclopent-2-en-1-one | 2-(6-carboxy-5-oxahexyl)-3-[2-hydroxy-3-(4-fluorophenoxypropylthio]cyclopentanone |
| 76 | 34 | 2-(6-carboxy-5-oxahexyl)-cyclopent-2-en-1-one | 2-(6-carboxy-5-oxahexyl)-3-[2-hydroxy-3-(3-trifluoromethylphenoxy)propylthio]-cyclopentanone |
| 77 | 35 | 2-(6-carboxy-5-oxahexyl)-cyclopent-2-en-1-one | 2-(6-carboxy-5-oxahexyl)-3-[2-hydroxy-3-(3-chlorophenoxy)propylthio]cyclopentanone |
| 78 | 42 | 2-(6-carboxy-5-oxahexyl)-cyclopent-2-en-1-one | 2-(6-carboxy-5-oxahexyl)-3-[2-hydroxy-3-(4-bromophenoxy)propylthio]cyclopentanone |
| 79 | 43 | 2-(6-carboxy-5-oxahexyl)-cyclopent-2-en-1-one | 2-(6-carboxy-5-oxahexyl)-3-(2-hydroxy-heptylthio)cyclopentanone |
| 80 | 44 | 2-(6-carboxy-5-oxahexyl)-cyclopent-2-en-1-one | 2-(6-carboxy-5-oxahexyl)-3-(2-hydroxy-hexylthio)cyclopentanone |
| 81 | 33 | 2-(6-carboxy-5-thiahexyl)-cyclopent-2-en-1-one | 2-(6-carboxy-5-thiahexyl)-3-[2-hydroxy-3-(4-fluorophenoxy)propylthio]cyclopentanone |
| 82 | 34 | 2-(6-carboxy-5-thiahexyl)-cyclopent-2-en-1-one | 2-(6-carboxy-5-thiahexyl)-3-[2-hydroxy-3-(3-trifluoromethylphenoxy)propylthio]-cyclopentanone |
| 83 | 35 | 2-(6-carboxy-5-thiahexyl)-cyclopent-2-en-1-one | 2-(6-carboxy-5-thiahexyl)-3-[2-hydroxy-3-(3-chlorophenoxy)propylthio]cyclopentanone |
| 84 | 36 | 2-(6-carboxy-5-thiahexyl)-cyclopent-2-en-1-one | 2-(6-carboxy-5-thiahexyl)-3-[2-hydroxy-3-(2-methylphenoxy)propylthio]cyclopentanone |
| 85 | 43 | 2-(6-carboxy-5-thiahexyl)-cyclopent-2-en-1-one | 2-(6-carboxy-5-thiahexyl)-3-(2-hydroxy-heptylthio)cyclopentanone |

TABLE VII-continued

| Example | 1-mercapto-2-hydroxy compound of Example | Starting cyclopentenone | Product |
|---|---|---|---|
| 86 | 45 | 2-(6-carboxy-5-thiahexyl)-cyclopent-2-en-1-one | 2-(6-carboxy-5-thiahexyl)-3-(2-hydroxy-octylthio)cyclopentanone |
| 87 | 33 | 2-(6-carboxyhex-2-cis-enyl)-cyclopent-2-en-1-one | 2-(6-carboxyhex-2-cis-enyl)-3-[2-hydroxy-3-(4-fluorophenoxy)propylthio]cyclopentanone |
| 88 | 34 | 2-(6-carboxyhex-2-cis-enyl)-cyclopent-2-en-1-one | 2-(6-carboxyhex-2-cis-enyl)-3-[2-hydroxy-3-(3-trifluoromethylphenoxy)propylthio]-cyclopentanone |
| 89 | 35 | 2-(6-carboxyhex-2-cis-enyl)-cyclopent-2-en-1-one | 2-(6-carboxyhex-2-cis-enyl)-3-[2-hydroxy-3-(3-chlorophenoxy)pentanone |
| 90 | 37 | 2-(6-carboxyhex-2-cis-enyl)-cyclopent-2-en-1-one | 2-(6-carboxyhex-2-cis-enyl)-3-[2-hydroxy-3-(3-methoxyphenoxy)propylthio]cyclopentanone |
| 91 | 43 | 2-(6-carboxyhex-2-cis-enyl)-cyclopent-2-en-1-one | 2-(6-carboxyhex-2-cis-enyl)-3-(2-hydroxy-heptylthio)cyclopentanone |
| 92 | 44 | 2-(6-carboxyhex-2-cis-enyl)-cyclopent-2-en-1-one | 2-(6-carboxyhex-2-cis-enyl)-3-(2-hydroxy-hexylthio)cyclopentanone |
| 93 | 33 | 2-(5-carboxypentyl)cyclopent-2-en-1-one | 2-(5-carboxypentyl)-3-[2-hydroxy-3-(4-fluorophenoxy)propylthio]cyclopentanone |
| 94 | 34 | 2-(5-carboxypentyl)cyclopent-2-en-1-one | 2-(5-carboxypentyl)-3-[2-hydroxy-3-(3-trifluoromethylphenoxy)propylthio]cyclopentanone |
| 95 | 35 | 2-(5-carboxypentyl)cyclopent-2-en-1-one | 2-(5-carboxypentyl)-3-[2-hydroxy-3-(3-chlorophenoxy)propylthio]cyclopentanone |
| 96 | 38 | 2-(5-carboxypentyl)cyclopent-2-en-1-one | 2-(5-carboxypentyl)-3-[2-hydroxy-3-(3,4-dichlorophenoxy)propylthio]cyclopentanone |
| 97 | 33 | 2-(7-carboxyheptyl)cyclopent-2-en-1-one | 2-(7-carboxyheptyl)-3-[2-hydroxy-3-(4-fluorophenoxy)propylthio]cyclopentanone |
| 98 | 34 | 2-(7-carboxyheptyl)cyclopent-2-en-1-one | 2-(7-carboxyheptyl)-3-[2-hydroxy-3-(3-trifluoromethylphenoxy)propylthio]cyclopentanone |
| 99 | 35 | 2-(7-carboxyheptyl)cyclopent-2-en-1-one | 2-(7-carboxyheptyl)-3-[2-hydroxy-3-(3-chlorophenoxy)propylthio]cyclopentanone |
| 100 | 39 | 2-(7-carboxyheptyl)cyclopent-2-en-1-one | 2-(7-carboxyheptyl)-3-[hydroxy-3-(3-fluorophenoxy)propylthio]cyclopentanone |
| 101 | 33 | 2-(8-carboxyoctyl)cyclopent-2-en-1-one | 2-(8-carboxyoctyl)-3-[2-hydroxy-3-(4-fluorophenoxy)propylthio]cyclopentanone |
| 102 | 34 | 2-(8-carboxyoctyl)cyclopent-2-en-1-one | 2-(8-carboxyoctyl)-3-[2-hydroxy-3-(3-trifluoromethylphenoxy)propylthio]cyclopentanone |
| 103 | 35 | 2-(8-carboxyoctyl)cyclopent-2-en-1-one | 2-(8-carboxyoctyl)-3-[2-hydroxy-3-(3-chlorophenoxy)propylthio]cyclopentanone |
| 104 | 40 | 2-(8-carboxyoctyl)cyclopent-2-en-1-one | 2-(8-carboxyoctyl)-3-[2-hydroxy-3-(4-chlorophenoxy)propylthio]cyclopentanone |

EXAMPLE 105

Preparation of 2-(6-carboxhex-2-cis-enyl)-3-(2-hydroxyheptylthio)-4-hydroxycyclopentanone To 2.5 g. (0.0112 mol) of 2-(6-carboxyhex-2-cis-enyl)-4-hydroxycyclopent-2-en-1-one is added 2.25 g. (0.0152 mol) of 1-mercapto-2-hydroxyheptane and 1.12 g. (0.0112 mol) of triethylamine. The reagents are mixed as a mild exothermic reaction ensues. After standing for 35 minutes at room temperature, the resulting oil is washed with ether and then mixed with ether and dilute hydrochloric acid. The ether layer is washed with water followed by a saturated solution of sodium chloride. The ether solution is dried over magnesium sulfate and treated with Norite. The ether is removed to give 3.97 g. of an oil which is chromatographed on a dry column of silica gel eluting with ether containing 1% acetic acid to give 2.68 g. (0.0072 mol) of 2-(6-carboxyhex-2-cis-enyl)-3-(2-hydroxyheptylthio)-4-hydroxy-cyclopentanone.

IR: neat, 3390 (OH), 1710, 1724, 1730 (carbonyls) cm$^{-1}$. NMR: $\delta_{TMS}^{CDCl_3}$, 5.46 (m, 2H, vinyl), 4.50 (bs, 3H, OH), 4.35 (m, 1H, C$\underline{H}$OCH in cyclopentanone), 3.77 (m, 1H, C$\underline{H}$OH, B to sulfur), 3.30 –1.60 (ms, 12H, allylic, protons α to carbonyls and sulfur), 1.30 (m, 10H, methylenes), 0.90 (m, 3H, terminal methyl).

MS: m/c, 354 (m—H$_2$O).

EXAMPLES 106–174

By the procedure described in Example 105, the various 4-hydroxycyclopentanones listed in Table VIII are prepared.

TABLE VIII

| Example | 1-mercapto-2-hydroxy compound of Example | Starting 2-hydroxy cyclopentenone | Product |
|---|---|---|---|
| 106 | 34 | 2-(6-carboxyhex-2-cis-enyl)-4-hydroxycyclopent-2-en-1-one | 2-(6-carboxyhex-2-cis-enyl)-3-[2-hydroxy-3-(3-trifluoromethylphenoxy)propylthio]-4-hydroxycyclopentanone |
| 107 | 35 | 2-(6-carboxyhex-2-cis-enyl)-4-hydroxycyclopent-2-en-1-one | 2-(6-carboxyhex-2-cis-enyl)-3-[2-hydroxy-3-(3-chlorophenoxy)propylthio]-4-hydroxy- |

TABLE VIII-continued

| Example | 1-mercapto-2-hydroxy compound of Example | Starting 2-hydroxy cyclopentenone | Product |
|---|---|---|---|
| | | | cyclopentanone |
| 108 | 36 | 2-(6-carboxyhex-2-cis-enyl)-4-hydroxycyclopent-2-en-1-one | 2-(6-carboxyhex-2-cis-enyl)-3-[2-hydroxy-3-(2-methylphenoxy)propylthio]-4-hydroxycyclopentanone |
| 109 | 33 | 2-(6-carboxyhex-2-cis-enyl)-4-hydroxycyclopent-2-en-1-one | 2-(6-carboxyhex-2-cis-enyl)-3-[2-hydroxy-3-(4-fluorophenoxy)propylthio]-4-hydroxycyclopentanone |
| 110 | 45 | 2-(6-carboxyhex-2-cis-enyl)-4-hydroxycyclopent-2-en-1-one | 2-(6-carboxyhex-2-cis-enyl)-3-(2-hydroxyoctylthio)-4-hydroxycyclopentanone |
| 111 | 33 | 2-(4-methyl-6-carboxyhex-2-cis-enyl)-4-hydroxycyclopent-2-en-1-one | 2-(4-methyl-6-carboxyhex-2-cis-enyl)-3-[2-hydroxy-3-(4-fluorophenoxy)propylthio]-4-hydroxycyclopentanone |
| 112 | 34 | 2-(4-methyl-6-carboxyhex-2-cis-enyl)-4-hydroxycyclopent-2-en-1-one | 2-(4-methyl-6-carboxyhex-2-cis-enyl)-3-[2-hydroxy-3-(3-trifluoromethylphenoxy)propylthio]-4-hydroxycyclopentanone |
| 113 | 35 | 2-(4-methyl-6-carboxyhex-2-cis-enyl)-4-hydroxycyclopent-2-en-1-one | 2-(4-methyl-6-carboxyhex-2-cis-enyl)-3-[2-hydroxy-3-(3-chlorophenoxy)propylthio]-4-hydroxycyclopentanone |
| 114 | 39 | 2-(4-methyl-6-carboxyhex-2--cis-enyl)-4-hydroxycyclopent-2-en-1-one | 2-(4-methyl-6-carboxyhex-2-cis-enyl)-3-[2-hydroxy-3-(3-fluorophenoxy)propylthio]-4-hydroxycyclopentanone |
| 115 | 43 | 2-(4-methyl-6-carboxyhex-2-cis-enyl)-4-hydroxycyclopent-2-en-1-one | 2-(4-methyl-6-carboxyhex-2-cis-enyl)-3-(2-hydroxyheptylthio)-4-hydroxycyclopentanone |
| 116 | 44 | 2-(4-methyl-6-carboxyhex-2-cis-enyl)-4-hydroxycyclopent-2-en-1-one | 2-(4-methyl-6-carboxyhex-2-cis-enyl)-3-(2-hydroxyhexylthio)-4-hydroxycyclopentanone |
| 117 | 33 | 2-(4-propyl-6-carboxyhex-2-cis-enyl)-4-hydroxycyclopent-2-en-1-one | 2-(4-propyl-6-carboxyhex-2-cis-enyl)-3-[2-hydroxy-3-(4-fluorophenoxy)propylthio]-4-hydroxycyclopentanone |
| 118 | 34 | 2-(4-propyl-6-carboxyhex-2-cis-enyl)-4-hydroxycyclopent-2-en-1-one | 2-(4-propyl-6-carboxyhex-2-cis-enyl)-3-[2-hydroxy-3-(3-trifluoromethylphenoxy)propylthio]-4-hydroxycyclopentanone |
| 119 | 35 | 2-(4-propyl-6-carboxyhex-2-cis-enyl)-4-hydroxycyclopent-2-en-1-one | 2-(4-propyl-6-carboxyhex-2-cis-enyl)-3-[2-hydroxy-3-(3-chlorophenoxy)propylthio]-4-hydroxycyclopentanone |
| 120 | 40 | 2-(6-carboxyhex-2-cis-enyl)-4-hydroxycyclopent-2-en-1-one | 2-(6-carboxyhex-2-cis-enyl)-3-[2-hydroxy-3-(4-chlorophenoxy)propylthio]-4-hydroxycyclopentanone |
| 121 | 43 | 2-(4-propyl-6-carboxyhex-2-cis-enyl)-4-hydroxycyclopent-2-en-1-one | 2-(4-propyl-6-carboxyhex-2-cis-enyl)-3-(2-hydroxyheptlthio)-4-hydroxycyclopentanone |
| 122 | 45 | 2-(4-propyl-6-carboxyhex-2-cis-enyl)-4-hydroxycyclopent-2-en-1-one | 2-(4-propyl-6-carboxyhex-2-cis-enyl)-3-(2-hydroxyoctylthio)-4-hydroxycyclopentanone |
| 123 | 33 | 2-(6-carboxy-5-oxahexyl)-4-hydroxycyclopent-2-en-1-one | 2-(6-carboxy-5-oxahexyl)-3-[2-hydroxy-3-(4-fluorophenoxy)propylthio]-4-hydroxycyclopentanone |
| 124 | 34 | 2-(6-carboxy-5-oxahexyl)-4-hydroxycyclopent-2-en-1-one | 2-(6-carboxy-5-oxahexyl)-3-[2-hydroxy-3-(3-trifluoromethylphenoxy)propylthio]-4-hydroxycyclopentanone |
| 125 | 35 | 2-(6-carboxy-5-oxahexyl)-4-hydroxycyclopent-2-en-1-one | 2-(6-carboxy-5-oxahexyl)-3-[2-hydroxy-3-[2-hydroxy-3-(3-chlorophenoxy)propylthio]-4-hydroxycyclopentanone |
| 126 | 41 | 2-(6-carboxy-5-oxahexyl)-4-hydroxycyclopent-2-en-1-one | 2-(6-carboxy-5-oxahexyl)-3-[2-hydroxy-3-(2-chloro-4-methylphenoxy)propylthio]-4-hydroxycyclopentanone |
| 127 | 43 | 2-(6-carboxy-5-oxahexyl)-4-hydroxycyclopent-2-en-1-one | 2-(6-carboxy-5-oxahexyl)-3-(2-hydroxyheptylthio)-4-hydroxycyclopentanone |
| 128 | 44 | 2-(6-carboxy-5-oxahexyl)-4-hydroxycyclopent-2-en-1-one | 2-(6-carboxy-5-oxahexyl)-3-(2-hydroxyhexylthio)-4-hydroxycyclopentanone |
| 129 | 33 | 2-(5,5-dimethyl-6-carboxyhexyl)-4-hydroxycyclopent-2-en-1-one | 2-(5,5-dimethyl-6-carboxyhexyl)-3-[2-hydroxy-3-(4-fluorophenoxy)propylthio]-4-hydroxycyclopentanone |
| 130 | 34 | 2-(5,5-dimethyl-6-carboxyhexyl)-4-hydroxycyclopent-2-en-1-one | 2-(5,5-dimethyl-6-carboxyhexyl)-3-[2-hydroxy-3-(3-trifluoromethylphenoxy)propylthio]-4-hydroxycyclopentanone |
| 131 | 35 | 2-(5,5-dimethyl-6-carboxyhexyl)-4-hydroxycyclopent-2-en-1-one | 2-(5,5-dimethyl-6-carboxyhexyl)-3-[2-hydroxy-3-(3-chlorophenoxy)propylthio]-4-hydroxycyclopentanone |
| 132 | 42 | 2-(5,5-dimethyl-6-carboxyhexyl)-4-hydroxycyclopent-2-en-1-one | 2-(5,5-dimethyl-6-carboxyhexyl)-3-[2-hydroxy-3-(4-bromophenoxy)propylthio]-4-hydroxycyclopentanone |
| 133 | 43 | 2-(5,5-dimethyl-6-carboxyhexyl)-4-hydroxycyclopent-2-en-1-one | 2-(5,5-dimethyl-6-carboxyhexyl)-3-(2-hydroxyheptylthio)-4-hydroxycyclopentanone |
| 134 | 45 | 2-(5,5-dimethyl-6-carboxyhexyl)-4-hydroxycyclopent-2-en-1-one | 2-(5,5-dimethyl-6-carboxyhexyl)-3-(2-hydroxyoctylthio)-4-hydroxycyclopentanone |

TABLE VIII-continued

| Example | 1-mercapto-2-hydroxy compound of Example | Starting 2-hydroxy cyclopentenone | Product |
| --- | --- | --- | --- |
| 135 | 33 | 2-(5-carboxypent-2-cis-enyl)-4-hydroxycyclopent-2-en-1-one | 2-(5-caboxypent-2-cis-enyl)-3-[2-hydroxy-3-(4-fluorophenoxy)propylthio]-4-hydroxycyclopentanone |
| 136 | 34 | 2-(5-carboxypent-2-cis-enyl)-4-hydroxycyclopent-2-en-1-one | 2-(5-carboxypent-2-cis-enyl)-3-[2-hydroxy-3-(3-trifluoromethylphenoxy)propylthio]-4-hydroxycyclopentanone |
| 137 | 35 | 2-(5-carboxypent-2-cis-enyl)-4-hydroxycyclopent-2-en-1-one | 2-(5-carboxypent-2-cis-enyl)-3-[2-hydroxy-3-(3-chlorophenoxy)propylthio]-4-hydroxycyclopentanone |
| 138 | 42 | 2-(5-carboxypent-2-cis-enyl)-4-hydroxycyclopent-2-en-1-one | 2-(5-carboxypent-2-cis-enyl)-3-[2-hydroxy-3-(4-bromophenoxy)propylthio]-4-hydroxycyclopentanone |
| 139 | 43 | 2-(5-carboxypent-2-cis-enyl)-4-hydroxycyclopent-2-en-1-one | 2-(5-carboxypent-2-cis-enyl)-3-(2-hydroxyheptylthio)-4-hydroxycyclopentanone |
| 140 | 44 | 2-(5-carboxypent-2-cis-enyl)-4-hydroxycyclopent-2-en-1-one | 2-(5-carboxypent-2-cis-enyl)-3-(2-hydroxyhexylthio)-4-hydroxycyclopentanone |
| 141 | 33 | 2-(7-carboxyhept-2-cis-enyl)-4-hydroxycyclopent-2-en-1-one | 2-(7-carboxyhept-2-cis-enyl)-3-[2-hydroxy-3-(4-fluorophenoxy)propylthio]-4-hydroxycyclopentanone |
| 142 | 34 | 2-(7-carboxyhept-2-cis-enyl)-4-hydroxycyclopent-2-en-1-one | 2-(7-carboxyhept-2-cis-enyl)-3-[2-hydroxy-3-(3-trifluoromethylphenoxy)propylthio]-4-hydroxycyclopentanone |
| 143 | 35 | 2-(7-carboxyhept-2-cis-enyl)-4-hydroxycyclopent-2-en-1-one | 2-(7-carboxyhept-2-cis-enyl)-3-[2-hydroxy-3-(3-chlorophenoxy)propylthio]-4-hydroxycyclopentanone |
| 144 | 36 | 2-(7-carboxyhept-2-cis-enyl)-4-hydroxycyclopent-2-en-1-one | 2-(7-carboxyhept-2-cis-enyl)-3-[2-hydroxy-3-(2-methylphenoxy)propylthio]-4-hydroxycyclopentanone |
| 145 | 43 | 2-(7-carboxyhept-2-cis-enyl)-4-hydroxycyclopent-2-en-1-one | 2-(7-carboxyhept-2-cis-enyl)-3-(2-hydroxyheptylthio)-4-hydroxycyclopentanone |
| 146 | 45 | 2-(7-carboxyhept-2-cis-enyl)-4-hydroxycyclopent-2-en-1-one | 2-(7-carboxyhept-2-cis-enyl)-3-(2-hydroxyoctylthio)-4-hydroxycyclopentanone |
| 147 | 33 | 2-(6-methyl-6-carboxyhexyl)-4-hydroxycyclopent-2-en-1-one | 2-(6-methyl-6-carboxyhexyl)-3-[2-hydroxy-3-(4-fluorophenoxy)propylthio]-4-hydroxycyclopentanone |
| 148 | 34 | 2-(6-methyl-6-carboxyhexyl)-4-hydroxycyclopent-2-en-1-one | 2-(6-methyl-6-carboxyhexyl)-3-[2-hydroxy-3-(3-trifluoromethylphenoxy)propylthio]-4-hydroxycyclopentanone |
| 149 | 35 | 2-(6-methyl-6-carboxyhexyl)-4-hydroxycyclopent-2-en-1-one | 2-(6-methyl-6-carboxyhexyl)-3-[2-hydroxy-3-(3-chlorophenoxy)propylthio]-4-hydroxycyclopentanone |
| 150 | 38 | 2-(6-methyl-6-carboxyhexyl)-4-hydroxycyclopent-2-en-1-one | 2-(6-methyl-6-carboxyhexyl)-3-[2-hydroxy-3-(3,4-dichlorophenoxy)propylthio]-4-hydroxycyclopentanone |
| 151 | 43 | 2-(6-methyl-6-carboxyhexyl)-4-hydroxycyclopent-2-en-1-one | 2-(6-methyl-6-carboxyhexyl)-3-(2-hydroxyheptylthio)-4-hydroxycyclopentanone |
| 152 | 44 | 2-(6-methyl-6-carboxyhexyl)-4-hydroxycyclopent-2-en-1-one | 2-(6-methyl-6-carboxyhexyl)-3-(2-hydroxyhexylthio)-4-hydroxycyclopentanone |
| 153 | 33 | 2-(6-ethyl-6-carboxyhexyl)-4-hydroxycyclopent-2-en-1-one | 2-(6-ethyl-6-carboxyhexyl-3-[2-hydroxy-3-(4-flurophenoxy)propylthio]-4-hydroxycyclopentanone |
| 154 | 34 | 2-(6-ethyl-6-carboxyhexyl)-4-hydroxycyclopent-2-en-1-one | 2-(6-ethyl-6-carboxyhexyl)-3-[2-hydroxy-3-(3-trifluoromethylphenoxy)propylthio]-4-hydroxycyclopentanone |
| 155 | 35 | 2-(6-ethyl-6-carboxyhexyl)-4-hydroxycyclopent-2-en-1-one | 2-(6-ethyl-6-carboxyhexyl)-3-[2-hydroxy-3-(3-chlorophenoxy)propylthio]-4-hydroxycyclopentanone |
| 156 | 39 | 2-(6-ethyl-6-carboxyhexyl)-4-hydroxycyclopent-2-en-1-one | 2-(6-ethyl-6-carboxyhexyl)-3-[2-hydroxy-3-(3-fluorophenoxy)propylthio]-4-hydroxycyclopentanone |
| 157 | 43 | 2-(6-ethyl-6-carboxyhexyl)-4-hydroxycyclopent-2-en-1-one | 2-(6-ethyl-6-carboxyhexyl)-3-(2-hydroxyheptylthio)-4-hydroxycyclopentanone |
| 158 | 45 | 2-(6-ethyl-6-carboxyhexyl)-4-hydroxycyclopent-2-en-1-one | 2-(6-ethyl-6-carboxyhexyl)-3-(2-hydroxyoctylthio)-4-hydroxycyclopentanone |
| 159 | 33 | 2-(6-carboxyhexyl)-4-hydroxycyclopent-2-en-1-one | 2-(6-carboxyhexyl)-3-[2-hydroxy-3-(4-fluorophenoxy)propylthio]-4-hydroxycyclopentanone |
| 160 | 34 | 2-(6-carboxyhexyl)-4-hydroxycyclopent-2-en-1-one | 2-(6-carboxyhexyl)-3-[2-hydroxy-3-(3-trifluoromethylphenoxy)propylthio]-4-hydroxycyclopentanone |
| 161 | 35 | 2-(6-carboxyhexyl)-4-hydroxycyclopent-2-en-1-one | 2-(6-carboxyhexyl)-3-[2-hydroxy-3-(3-chlorophenoxy)propylthio]-4-hydroxycyclopentanone |
| 162 | 40 | 2-(6-carboxyhexyl)-4-hydroxy-cyclopent-2-en-1-one | 2-(6-carboxyhexyl)-3-[2-hydroxy-3-(4-chlorophenoxy)propylthio]-4-hydroxycyclopentanone |
| 163 | 33 | 2-(5-carboxypentyl)-4- | 2-(5-carboxypentyl)-3-[2-hydroxy-3- |

TABLE VIII-continued

| Example | 1-mercapto-2-hydroxy compound of Example | Starting 2-hydroxy cyclopentenone | Product |
|---|---|---|---|
| | | hydroxy-cyclopent-2-en-1-one | (4-fluorophenoxy)propylthio]-4-hydroxy-cyclopentanone |
| 164 | 34 | 2-(5-carboxypentyl)-4-hydroxy-cyclopent-2-en-1-one | 2-(5-carboxypentyl)-3-[2-hydroxy-3-(3-trifluoromethylphenoxy)-propyl-thio]-4-hydroxycyclopentanone |
| 165 | 35 | 2-(5-carboxypentyl)-4-hydroxy-cyclopent-2-en-1-one | 2-(5-carboxypentyl)-3-[2-hydroxy-3-(3-chlorophenoxy)propylthio]-4-hydroxycyclopentanone |
| 166 | 41 | 2-(5-carboxypentyl)-4-hydroxy-cyclopent-2-en-1-one | 2-(5-carboxypentyl)-3-[2-hydroxy-3-(2-chloro-4-methylphenoxy)propylthio]-4-hydroxycyclopentanone |
| 167 | 33 | 2-(7-carboxyheptyl)-4-hydroxy-cyclopent-2-en-1-one | 2-(7-carboxyheptyl)-3-[2-hydroxy-3-(4-fluorophenoxy)propylthio]-4-hydroxy-cyclopentanone |
| 168 | 34 | 2-(7-carboxyheptyl)-4-hydroxy-cyclopent-2-en-1-one | 2-(7-carboxyheptyl)-3-[2-hydroxy-3-(3-trifluoromethylphenoxy)propylthio]-4-hydroxycyclopentanone |
| 169 | 35 | 2-(7-carboxyheptyl)-4-hydroxy-cyclopent-2-en-1-one | 2-(7-carboxyheptyl)-3-[2-hydroxy-3-(3-chlorophenoxy)propylthio]-4-hydroxy-cyclopentanone |
| 170 | 37 | 2-(7-carboxyheptyl)-4-hydroxy-cyclopent-2-en-1-one | 2-(7-carboxyheptyl)-3-[2-hydroxy-3-(3-methoxyphenoxy)propylthio]-4-hydroxy-cyclopentanone |
| 171 | 33 | 2-(8-carboxyoctyl)-4-hydroxy-cyclopent-2-en-1-one | 2-(8-carboxyoctyl)-3-[2-hydroxy-3-(4-fluorophenoxy)propylthio]-4-hydroxy-cyclopentanone |
| 172 | 34 | 2-(8-carboxyoctyl)-4-hydroxy-cyclopent-2-en-1-one | 2-(8-carboxyoctyl)-3-[2-hydroxy-3-(3-triflouromethylphenoxy)propylthio]-4-hydroxycyclopentanone |
| 173 | 35 | 2-(8-carboxyoctyl)-4-hydroxy-cyclopent-2-en-1-one | 2-(8-carboxyoctyl)-3-[2-hydroxy-3-(3-chlorophenoxy)propylthio]-4-hydroxy-cyclopentanone |
| 174 | 39 | 2-(8-carboxyoctyl)-4-hydroxy-cyclopent-2-en-1-one | 2-(8-carboxyoctyl)-3-[2-hydroxy-3-(3-fluorophenoxy)propylthio]-4-hydroxy-cyclopentanone |

EXAMPLE 175

Preparation of
2-(6-methyl-6-carbomethoxyhexyl)-3-(2-hydroxyheptylthio)cyclopentanone To a solution of 0.275 g. (0.738 mmol) of 2-(6-methyl-6-carboxyhexyl)-3-(2-hydroxyheptylthio) cyclopentanone in 10 ml. of ether is added an etheral solution of diazomethane till a permanent yellow color remains. The excess diazomethanes is destroyed by the addition of a drop of acetic acid. The solvent is removed at reduced pressure to give 0.28 g. (0.72 mmol) of 2-(6-methyl-6-carbomethoxyhexyl)-3-(2-hydroxyheptylthio)cyclopentanone.

IR: neat, 3510 (OH), 1740 (C=O) cm$^{-1}$.

EXAMPLES 176-193

By the procedure described in Example 175, the various esters listed in Table IX are prepared.

| Example | Acid of Example | Diazoalkane | Product Ester |
|---|---|---|---|
| 176 | 129 | 1-diazomethane | 2-(5,5-dimethyl-6-carbomethoxyhexyl)-3-[2-hydroxy-3-(4-fluorophenoxy)propylthio]-4-hydroxycyclopentanone |
| 177 | 136 | 1-diazohexane | 2-(5-carbohexoxypent-2-cis-enyl)-3-[2-hydroxy-3-(3-trifluoromethylphenoxy)propylthio]-4-hydroxycyclopentanone |
| 178 | 149 | 1-diazodecane | 2-(6-methyl-6-carbodecoxyhexyl)-3-[2-hydroxy-3-(3-chlorophenoxy)propylthio]-4-hydroxy-cyclopentanone |
| 179 | 159 | 2-diazopentane | 2-(6-carbo-(2-pentoxy)hexyl)-3-[2-hydroxy-3-(4-fluorophenoxy)propylthio]-4-hydroxycyclo-pentanone |
| 180 | 133 | diazomethane | 2-(5,5-dimethyl-6-carbomethoxyhexyl)-3-(2-hydroxyheptylthio)-4-hydroxycyclopentanone |
| 181 | 151 | diazoethane | 2-(6-methyl-6-carboethoxyhexyl)-3-(2-hydroxyheptylthio)-4-hydroxycyclopentanone |
| 182 | 109 | diazomethane | 2-(6-carbomethoxyhex-2-cis-enyl)-3-[2-hydroxy-3-(4-fluorophenoxy)propylthio]-4-hydroxy-cyclopentanone |
| 183 | 112 | 1-diazopentane | 2-(4-methyl-6-carbopentoxyhex-2-cis-enyl)-3-[2-hydroxy-3-(3-trifluoromethylphenoxy)-propylthio]-4-hydroxycyclopentanone |
| 184 | 107 | 1-diazodecane | 2-(6-carbodecoxyhex-2-cis-enyl)-3-[2-hydroxy-3-(3-chlorophenoxy)propylthio]-4-hydroxy-cyclopentanone |

-continued

| Example | Acid of Example | Diazoalkane | Product Ester |
|---|---|---|---|
| 185 | 117 | diazoethane | 2-(4-propyl-6-carboethoxyhex-2-cis-enyl)-3-[2-hydroxy-3-(4-fluorophenoxy)propylthio]-4-hydroxycyclopentanone |
| 186 | 105 | diazomethane | 2-(6-carbomethoxyhex-2-cis-enyl)-3-(2-hydroxyheptylthio)-4-hydroxycyclopentanone |
| 187 | 127 | 2-diazopropane | 2-(6-carbo(2-propoxy)-5-oxahexyl)-3-(2-hydroxyheptylthio)-4-hydroxycyclopentanone |
| 188 | 47 | diazomethane | 2-(6-methyl-6-carbomethoxyhexyl)-3-[2-hydroxy-3-(4-fluorophenoxy)propylthio]cyclopentanone |
| 189 | 53 | diazoethane | 2-(6-ethyl-6-carboethoxyhexyl)-3-[2-hydroxy-3(3-trifluoromethylphenoxy)propylthio]cyclopentanone |
| 190 | 60 | 1-diazooctane | 2-(6-phenyl-6-carbooctoxyhexyl)-3-[2-hydroxy-3-(3-chlorophenoxy)propylthio]cyclopentanone |
| 191 | 69 | 1-diazodecane | 2-(5,5-dimethyl-6-carbodecoxyhexyl)-3-[2-hydroxy-3-(4-fluorophenoxy)propylthio]cyclopentanone |
| 192 | 73 | diazomethane | 2-(5,5-dimethyl-6-carbomethoxyhexyl)-3-(2-hydroxyheptylthio)cyclopentanone |
| 193 | 194 | diazomethane | 2-(6-carbomethoxyhexyl-2-cis-enyl)-3-(2-hydroxyheptylthio)-1,4-dihydroxycyclopentane |

EXAMPLE 194

Preparation of 2-(6-carboxyhexyl-2-cis-enyl)-3-(2-hydroxyheptylthio)-1,4-dihydroxycyclopentane To a solution of 0.5 g. (1.34 mmol) of 2-(6-carboxyhex-2-cis-enyl)-3-(2-hydroxyheptylthio)-4-hydroxycyclopentanone in 7 ml. of ethanol is added with stirring at 0° C. 0.12 g. (3.17 mmol) of sodium borohydride. After stirring at room temperature for 2 hours, the ethanol is removed at reduced pressure. The residue is dissolved in a dilute solution of sodium bicarbonate. The aqueous solution is washed with ether and then acidified with dilute hydrochloric acid. The mixture is extracted with ether. The ether solution is dried over magnesium sulfate. The ether is removed and the residue is chromatographed on three 2000 mu silica gel plates which are developed with ethyl acetate, benzene 4:1 containing 2.5% acetic acid; 0.41 g. (1.09 mmol) of 2-(6-carboxyhex-2-cis-enyl)-3-(2-hydroxyheptylthio)-1,4-dihydroxycyclopentane.

IR: neat, 3330 (OH), 1710 ($CO_2H$) cm$^{-1}$.
MS: m/e, 356 (M-$H_2O$), 338 (M-2$H_2O$).
NMR: $\delta_{rms}^{CDl_3}$, 5.50 (m, 2H, vinyl), 4.60-3.30 (m's, 7H, α to OH,), 3.10−1.00 (m's, 22H, α to sulfur, methylenes, methine), 0.90 (m, 3H, terminal methyl).

EXAMPLES 195–321

By the procedure described in Example 194, the various hydroxy and dihydroxy cyclopentanes listed in Table X are prepared.

TABLE X

| Example | Cyclopentanone of Example | Product |
|---|---|---|
| 195 | 54 | 2-(6-ethyl-6-carboxyhexyl)-3-[2-hydroxy-3-(3-chlorophenoxy)propylthio]-1-hydroxycyclopentane |
| 196 | 55 | 2-(6-ethyl-6-carboxyhexyl)-3-[2-hydroxy-3-(3-methoxyphenoxy)propylthio]-1-hydroxycyclopentane |
| 197 | 56 | 2-(6-ethyl-6-carboxyhexyl)-3-(2-hydroxyoctylthio)-1-hydroxycyclopentane |
| 198 | 57 | 2-(6-ethyl-6-carboxyhexyl)-3-(2-hydroxyheptylthio)-1-hydroxycyclopentane |
| 199 | 58 | 2-(6-phenyl-6-carboxyhexyl)-3-[2-hydroxy-3-(4-fluorophenoxy)propylthio]-1-hydroxycyclopentane |
| 200 | 59 | 2-(6-phenyl-6-carboxyhexyl)-3-[2-hydroxy-3-(3-trifluoromethylphenoxy)propylthio]-1-hydroxycyclopentane |
| 201 | 60 | 2-(6-phenyl-6-carboxyhexyl)-3-[2-hydroxy-3-(3-chlorophenoxy)propylthio]-1-hydroxycyclopentane |
| 202 | 61 | 2-(6-phenyl-6-carboxyhexyl)-3-[2-hydroxy-3-(3,4-dichlorophenoxy)propylthio]-1-hydroxycyclopentane |
| 203 | 62 | 2-(6-phenyl-6-carboxyhexyl)-3-(2-hydroxyheptylthio)-1-hydroxycyclopentane |
| 204 | 63 | 2-(6-phenyl-6-carboxyhexyl)-3-(2-hydroxyhexylthio)-1-hydroxycyclopentane |
| 205 | 64 | 2-(6-carboxyhexyl)-3-[2-hydroxy-3-(4-fluorophenoxy)-propylthio]-1-hydroxycyclopentane |
| 206 | 65 | 2-(6-carboxyhexyl)-3-[2-hydroxy-3-(3-trifluoromethylphenoxy)propylthio]-1-hydroxycyclopentane |
| 207 | 66 | 2-(6-carboxyhexyl)-3-[2-hydroxy-3-(3-chlorophenoxy)propylthio]-1-hydroxycyclopentane |
| 208 | 67 | 2-(6-carboxyhexyl)-3-[2-hydroxy-3-(3-fluorophenoxy)propylthio]-1-hydroxycyclopentane |
| 209 | 68 | 2-(6-carboxyhexyl)-3-[2-hydroxy-3-(4-chloro |

TABLE X-continued

| Example | Cyclopentanone of Example | Product |
|---|---|---|
| 210 | 69 | phenoxy)propylthio]-1-hydroxycyclopentane 2-(5,5-dimethyl-6-carboxyhexyl)-3-[2-hydroxy-3-(4-fluorophenoxy)propylthio]-1-hydroxycyclopentane |
| 211 | 70 | 2-(5,5-dimethyl-6-carboxyhexyl)-3-[2-hydroxy-3-(3-trifluoromethylphenoxypropylthio]-1-hydroxycyclopentane |
| 212 | 71 | 2-(5,5-dimethyl-6-carboxyhexyl)-3-[2-hydroxy-3-(3-chlorophenoxy)propylthio]-1-hydroxycyclopentane |
| 213 | 72 | 2-(5,5-dimethyl-6-carboxyhexyl)-3-[2-hydroxy-3-(2-chloro-4-methylphenoxy)propylthio]-1-hydroxycyclopentane |
| 214 | 73 | 2-(5,5-dimethyl-6-carboxyhexyl)-3-(2-hydroxyheptylthio)-1-hydroxycyclopentane |
| 215 | 74 | 2-(5,5-dimethyl-6-carboxyhexyl)-3-(2-hydroxyoctylthio)-1-hydroxycyclopentane |
| 216 | 75 | 2-(6-carboxy-5-oxahexyl)-3-[2-hydroxy-3-(4-fluorophenoxy)propylthio]-1-hydroxycyclopentane |
| 217 | 76 | 2-(6-carboxy-5-oxahexyl)-3-[2-hydroxy-3-(3-trifluoromethylphenoxy)propylthio]-1-hydroxycyclopentane |
| 218 | 77 | 2-(6-carboxy-5-oxahexyl)-3-[2-hydroxy-3-(3-chlorophenoxy)propylthio]-1-hydroxycyclopentane |
| 219 | 78 | 2-(6-carboxy-5-oxahexyl)-3-[2-hydroxy-3-(4-bromophenoxy)propylthio]-1-hydroxycyclopentane |
| 220 | 79 | 2-(6-carboxy-5-oxahexyl)-3-(2-hydroxyheptylthio)-1-hydroxycyclopentane |
| 221 | 80 | 2-(6-carboxy-5-oxahexyl)-3-(2-hydroxyhexylthio)-1-hydroxycyclopentane |
| 222 | 81 | 2-(6-carboxy-5-thiahexyl)-3-[2-hydroxy-3-(4-fluorophenoxy)propylthio]-1-hydroxycyclopentane |
| 223 | 82 | 2-(6-carboxy-5-thiahexyl)-3-[2-hydroxy-3-(3-trifluoromethylphenoxy)propylthio]-1-hydroxycyclopentane |
| 224 | 83 | 2-(6-carboxy-5-thiahexyl)-3-[2-hydroxy-3-(3-chlorophenoxy)propylthio]-1-hydroxycyclopentane |
| 225 | 84 | 2-(6-carboxy-5-thiahexyl)-3-[2-hydroxy-3-(2-methylphenoxy)propylthio]-1-hydroxycyclopentane |
| 226 | 85 | 2-(6-carboxy-5-thiahexyl)-3-(2-hydroxyheptylthio)-1-hydroxycyclopentane |
| 227 | 86 | 2-(6-carboxy-5-thiahexyl)-3-(2-hydroxyoctylthio)-1-hydroxycyclopentane |
| 228 | 87 | 2-(6-carboxyhex-2-cis-enyl)-3-[2-hydroxy-3-(4-fluorophenoxy)propylthio]-1-hydroxycyclopentane |
| 229 | 88 | 2-(6-carboxyhex-2-cis-enyl)-3-[2-hydroxy-3-(3-trifluoromethylphenoxy)propylthio]-1-hydroxycyclopentane |
| 230 | 89 | 2-(6-carboxyhex-2-cis-enyl)-3-[2-hydroxy-3-(3-chlorophenoxy)propylthio]-1-hydroxycyclopentane |
| 231 | 90 | 2-(6-carboxyhex-2-cis-enyl)-3-[2-hydroxy-3-(3-methoxyphenoxy)propylthio]-1-hydroxycyclopentane |
| 232 | 91 | 2-(6-carboxyhex-2-cis-enyl)-3-(2-hydroxyheptylthio)-1-hydroxycyclopentane |
| 233 | 92 | 2-(6-carboxyhex-2-cis-enyl)-3-(2-hydroxyhexylthio)-1-hydroxycyclopentane |
| 234 | 93 | 2-(5-carboxypentyl)-3-[2-hydroxy-3-(4-fluorophenoxy)propylthio]-1-hydroxycyclopentane |
| 235 | 94 | 2-(5-carboxypentyl)-3-[2-hydroxy-3-(3-trifluoromethylphenoxy)propylthio]-1-hydroxycyclopentane |
| 236 | 95 | 2-(5-carboxypentyl)-3-[2-hydroxy-3-(3-chlorophenoxy)propylthio]-1-hydroxycyclopentane |
| 237 | 96 | 2-(5-carboxypentyl)-3-[2-hydroxy-3-(3,4-dichlorophenoxy)propylthio]-1-hydroxycyclopentane |
| 238 | 97 | 2-(7-carboxyheptyl)-3-[2-hydroxy-3-(4-fluorophenoxy)propylthio]-1-hydroxycyclopentane |
| 239 | 98 | 2-(7-carboxyheptyl)-3-[2-hydroxy-3-(3-trifluoromethylphenoxy)propylthio]-1-hydroxycyclopentane |
| 240 | 99 | 2-(7-carboxyheptyl)-3-[2-hydroxy-3-(3-chlorophenoxy)propylthio]-1-hydroxycyclopentane |
| 241 | 100 | 2-(7-carboxyheptyl)-3-[2-hydroxy-3-(3-fluorophenoxy)propylthio]-1-hydroxycyclopentane |
| 242 | 101 | 2-(8-carboxyoctyl)-3-[2-hydroxy-3-(4-fluorophenoxy)propylthio]-1-hydroxycyclopentane |
| 243 | 102 | 2-(8-carboxyoctyl)-3-[2-hydroxy-3-(3-trifluoromethylphenoxy)propylthio]-1-hydroxycyclopentane |
| 244 | 103 | 2-(8-carboxyoctyl)-3-[2-hydroxy-3-(3-chloro- |

TABLE X-continued

| Example | Cyclopentanone of Example | Product |
|---|---|---|
| 245 | 104 | phenoxy)propylthio]-1-hydroxycyclopentane 2-(8-carboxyoctyl)-3-[2-hydroxy-3-(4-chlorophenoxy)propylthio]-1-hydroxycyclopentane |
| 246 | 106 | 2-(6-carboxyhex-2-cis-enyl)-3-[2-hydroxy-3-(3-trifluoromethylphenoxy)propylthio]-1,4-dihydroxycyclopentane |
| 247 | 107 | 2-(6-carboxyhex-2-cis-enyl)-3-[2-hydroxy-3-(3-chlorophenoxy)propylthio]-1,4-dihydroxycyclopentane |
| 248 | 108 | 2-(6-carboxyhex-2-cis-enyl)-3-[2-hydroxy-3-(2-methylphenoxy)propylthio]-1,4-dihydroxycyclopentane |
| 249 | 109 | 2-(6-carboxyhex-2-cis-enyl)-3-[2-hydroxy-3-(4-fluorophenoxy)propylthio]-1,4-dihydroxycyclopentane |
| 250 | 110 | 2-(6-carboxyhex-2-cis-enyl)-3-(2-hydroxyoctylthio)-1,4-dihydroxycyclopentane |
| 251 | 117 | 2-(4-propyl-6-carboxyhex-2-cis-enyl)-3-[2-hydroxy-3-(4-fluorophenoxy)propylthio]-1,4-dihydroxycyclopentane |
| 252 | 118 | 2-(4-propyl-6-carboxyhex-2-cis-enyl)-3-[2-hydroxy-3-(3-trifluoromethylphenoxy)propylthio]-1,4-dihydroxycyclopentane |
| 253 | 119 | 2-(4-propyl-6-carboxyhex-2-cis-enyl)-3-[2-hydroxy-3-(3-chlorophenoxy)propylthio]-1,4-dihydroxycyclopentane |
| 254 | 120 | 2-(6-carboxyhex-2-cis-enyl)-3-[2-hydroxy-3-(4-chlorophenoxy)propylthio]-1,4-dihydroxycyclopentane |
| 255 | 121 | 2-(4-propyl-6-carboxyhex-2-cis-enyl)-3-(2-hydroxyheptylthio)-1,4-dihydroxycyclopentane |
| 256 | 122 | 2-(4-propyl-6-carboxyhex-2-cis-enyl)-3-(2-hydroxyoctylthio)-1,4-dihydroxycyclopentane |
| 257 | 123 | 2-(6-carboxy-5-oxahexyl)-3-[2-hydroxy-3-(4-fluorophenoxy)propylthio]-1,4-dihydroxycyclopentane |
| 258 | 124 | 2-(6-carboxy-5-oxahexyl)-3-[2-hydroxy-3-(3-trifluoromethylphenoxy)propylthio]-1,4-dihydroxycyclopentane |
| 259 | 125 | 2-(6-carboxy-5-oxahexyl)-3-[2-hydroxy-3-(3-chlorophenoxy)propylthio]-1,4-dihydroxycyclopentane |
| 260 | 126 | 2-(6-carboxy-5-oxahexyl)-3-[2-hydroxy-3-(2-chloro-4-methylphenoxy)propylthio]-1,4-dihydroxycyclopentane |
| 261 | 127 | 2-(6-carboxy-5-oxahexyl)-3-(2-hydroxyheptylthio)-1,4-dihydroxycyclopentane |
| 262 | 128 | 2-(6-carboxy-5-oxahexyl)-3-(2-hydroxyhexylthio)-1,4-dihydroxycyclopentane |
| 263 | 129 | 2-(5,5-dimethyl-6-carboxyhexyl)-3-[2-hydroxy-3-(4-fluorophenoxy)propylthio]-1,4-dihydroxycyclopentane |
| 264 | 130 | 2-(5,5-dimethyl-6-carboxyhexyl)-3-[2-hydroxy-3-(3-trifluoromethylphenoxy)propylthio]-1,4-dihydroxycyclopentane |
| 265 | 131 | 2-(5,5-dimethyl-6-carboxyhexyl)-3-[2-hydroxy-3-(3-chlorophenoxy)propylthio]-1,4-dihydroxycyclopentane |
| 266 | 132 | 2-(5,5-dimethyl-6-carboxyhexyl)-3-[2-hydroxy-3-(4-bromophenoxy)propylthio]-1,4-dihydroxycyclopentane |
| 267 | 133 | 2-(5,5-dimethyl-6-carboxyhexyl)-3-(2-hydroxyheptylthio)-1,4-dihydroxycyclopentane |
| 268 | 134 | 2-(5,5-dimethyl-6-carboxyhexyl)-3-(2-hydroxyoxtylthio)-1,4-dihydroxycyclopentane |
| 269 | 135 | 2-(5-carboxypent-2-cis-enyl)-3-[2-hydroxy-3-(4-fluorophenoxy)propylthio]-1,4-dihydroxycyclopentane |
| 270 | 136 | 2-(5-carboxypent-2-cis-enyl)-3-[2-hydroxy-3-(3-trifluoromethylphenoxy)propylthio]-1,4-dihydroxycyclopentane |
| 271 | 137 | 2-(5-carboxypent-2-cis-enyl)-3-[2-hydroxy-3-(3-chlorophenoxy)propylthio]1,4-dihydroxycyclopentane |
| 272 | 138 | 2-(5-carboxypent-2-cis-enyl)-3-[2-hydroxy-3-(4-bromophenoxy)propylthio]-1,4-dihydroxycyclopentane |
| 273 | 139 | 2-(5-carboxypent-2-cis-enyl)-3-(2-hydroxyheptylthio)-1,4-dihydroxycyclopentane |
| 274 | 140 | 2-(5-carboxypent-2-cis-enyl)-3-(2-hydroxyhexylthio)-1,4-dihydroxycyclopentane |
| 275 | 141 | 2-(7-carboxyhept-2-cis-3-[2-hydroxy-3-(4-fluorophenoxy)propylthio]-1,4-dihydroxycyclopentane |
| 276 | 142 | 2-(7-carboxyhept-2-cis-enyl)-3-[2-hydroxy-3-(3-trifluoromethylphenoxy)propylthio]-1,4-dihydroxycyclo- |

TABLE X-continued

| Example | Cyclopentanone of Example | Product |
|---|---|---|
| 277 | 143 | 2-(7-carboxyhept-2-cis-enyl)-3-[2-hydroxy-3-(3-chlorophenoxy)-propylthio]-1,4-dihydroxycyclopentane |
| 278 | 144 | 2-(7-carboxyhept-2-cis-enyl)-3-[2-hydroxy-3-(2-methylphenoxy)-propylthio]-1,4-dihydroxycyclopentane |
| 279 | 145 | 2-(7-carboxyhept-2-cis-enyl)-3-(2-hydroxy-heptylthio)-1,4-dihydroxycyclopentane |
| 280 | 146 | 2-(7-carboxyhept-2-cis-enyl)-3-(2-hydroxy-octylthio)-1,4-dihydroxycyclopentane |
| 281 | 147 | 2-(6-mehtyl-6-carboxy-hexyl)-3-[2-hydroxy-3-(4-fluorophenoxy)-propylthio]-1,4-dihydroxycyclopentane |
| 282 | 148 | 2-(6-methyl-6-carboxy-hexyl)-3-[2-hydroxy-3-3-trifluoromethyl-phenoxy)propylthio]-1,4-dihydroxycyclopentane |
| 283 | 149 | 2-(6-mehtyl-6-carboxy-hexyl)-3-[2-hydroxy-3-(3-chlorophenoxy)propylthio]-1,4-dihydroxycyclopentane |
| 284 | 150 | 2-(6-methyl-6-carboxy-hexyl)-3-[2-hydroxy-3-(3,4-dichlorophenoxy)-propylthio]-1,4-dihydroxycyclopentane |
| 285 | 151 | 1-(6-methyl-6-carboxy-hexyl)-3-(2-hydroxy-heptylthio)-1,4-dihydroxycyclopentane |
| 286 | 152 | 2-(6-methyl-6-carboxy-hexyl)-3-(2-hydroxy-hexylthio)-1,4-dihydroxycyclopentane |
| 287 | 153 | 2-(6-ethyl-6-carboxy-hexyl)-3-[2-hydroxy-3-(4-fluorophenoxy-propylthio]-1,4-dihydroxycyclopentane |
| 288 | 154 | 2-(6-ethyl-6-carboxy-hexyl)-3-[2-hydroxy-3-(3-trifluoromethyl-phenoxy)propylthio]-1,4-dihydroxycyclopentane |
| 289 | 155 | 2-(6-ethyl-6-carboxy-hexyl)-3-[2-hydroxy-3-(3-chlorophenoxy)-propylthio]-1,4-dihydroxycyclopentane |
| 290 | 156 | 2-(6-ethyl-6-carboxy-hexyl)-3-[2-hydroxy-3-(3-fluorophenoxy)-propylthio]-1,4-dihydroxycyclopentane |
| 291 | 157 | 2-(6-ethyl-6-carboxy-hexyl)-3-(2-hydroxy-heptylthio)-1,4-dihydroxycyclopentane |
| 292 | 158 | 2-(6-ethyl-6-carboxy-hexyl)-3-(2-hydroxy-octylthio)-1,4-dihydroxycyclopentane |
| 293 | 159 | 2-(6-carboxyhexyl)-3-[2-hydroxy-3-(4-fluorophenoxy)propylthio]-1,4-dihydroxycyclopentane |
| 294 | 160 | 2-(6-carboxyhexyl)-3-[2-hydroxy-3-(3-trifluoromethylphenoxy)-propylthio]-1,4-dihydroxycyclopentane |
| 295 | 161 | 2-(6-carboxyhexyl)-3-[2-hydroxy-3-(3-chlorophenoxy)propylthio]-1,4-dihydroxycyclopentane |
| 296 | 162 | 2-(6-carboxyhexyl)-3-[2-hydroxy-3-(4-chlorophenoxy)-propylthio]-1,4-dihydroxycyclopentane |
| 297 | 163 | 2-(6-carboxypentyl)-3-[2-hydroxy-3-(4-fluorophenoxy)propylthio]-1,4-dihydroxycyclopentane |
| 298 | 164 | 2-(5-carboxypentyl)-3-[2-hydroxy-3-(3-trifluoromethylphenoxy)-propylthio]-1,4-dihydroxycyclopentane |
| 299 | 165 | 2-(5-carboxypentyl)-3-[2-hydroxy-3-(3-chlorophenoxy)propylthio]-1,4-dihydroxycyclopentane |
| 300 | 166 | 2-(5-carboxypentyl)-3-[2-hydroxy-3-(2-chloro-4-methylphenoxy)propylthio]-1,4-dihydroxycyclopentane |
| 301 | 167 | 2-(7-carboxyheptyl)-3-[2-hydroxy-3-(4-fluorophenoxy)propylthio]-1,4-dihydroxycyclopentane |
| 302 | 168 | 2-(7-carboxyheptyl)-3-[2-hydroxy-3-(3-trifluoromethylphenoxy)propylthio]-1,4-dihydroxycyclopentane |
| 303 | 169 | 2-(7-carboxyheptyl)-3-[2-hydroxy-3-(3-chlorophenoxy)propylthio]-1,4-dihydroxycyclopentane |
| 304 | 170 | 2-(7-carboxyheptyl)-3-[2-hydroxy-3-(3-methoxyphenoxy)propylthio]-1,4-dihydroxycyclopentane |
| 305 | 171 | 2-(8-carboxyoctyl)-3-[2-hydroxy-3-(4-fluorophenoxy)propylthio]-1,4-dihydroxycyclopentane |
| 306 | 172 | 2-(8-carboxyoctyl)-3-[2-hydroxy-3-(3-trifluoromethylphenoxy)-propylthio]-1,4-dihydroxycyclopentane |
| 307 | 173 | 2-(8-carboxyoctyl)-3-[2-hydroxy-3-(3-chlorophenoxy)propylthio]1,4-dihydroxycyclopentane |
| 308 | 174 | 2-(8-carboxyoctyl)-3-[2-hydroxy-3-(3-fluorophenoxy)propylthio]-1,4-dihydroxycyclopentane |
| 309 | 47 | 2-(6-methyl-6-carboxy-hexyl)-3-(2-hydroxy-3-(4-fluorophenoxy)-propylthio]-1-hydroxy- |

TABLE X-continued

| Example | Cyclopentanone of Example | Product |
|---|---|---|
| 310 | 48 | cyclopentane 2-(6-methyl-6-carboxyhexyl)-3-[2-hydroxy-3-(3-trifluoromethylphenoxy)propylthio]-1-hydroxycyclopentane |
| 311 | 49 | 2-(6-methyl-6-carboxyhexyl)-3-[2-hydroxy-3-(3-chlorophenoxy)-propylthio-1-hydroxycyclopentane |
| 312 | 50 | 2-(6-methyl-6-carboxyhexyl)-3-[2-hydroxy-3-(2-methylphenoxy)-propylthio]-1-hydroxycyclopentane |
| 313 | 51 | 2-(6-methyl-6-carboxyhexyl)-3-(2-hydroxyhexylthio)-1-hydroxycyclopentane |
| 314 | 52 | 2-(6-ethyl-6-carboxyhexyl)-3-[2-hydroxy-3-(4-fluorophenoxy)-propylthio]-1-hydroxycyclopentane |
| 315 | 53 | 2-(6-ethyl-6-carboxyhexyl)-3-[2-hydroxy-3-(3-trifluoromethylphenoxy)propylthio]-1-hydroxycyclopentane |
| 316 | 111 | 2-(4-methyl-6-carboxyhex-2-cis-enyl)-3-[2-hydroxy-3-(4-fluorophenoxy)propylthio]-1,4-dihydroxycyclopentane |
| 317 | 112 | 2-(4-methyl-6-carboxyhex-2-cis-enyl)-3-[2-hydroxy-3-(3-trifluoromethylphenoxy)propylthio]-1,4-dihydroxycyclopentane |
| 318 | 113 | 2-(4-methyl-6-carboxyhex-2-cis-enyl)-3-[2-hydroxy-3-(3-chlorophenoxy)propylthio]-1,4-dihdroxycyclopentane |
| 319 | 114 | 2-(4-methyl-6-carboxyhex-2-cis-enyl)-3-[2-hydroxy-3-(3-fluorophenoxy)propylthio]-1,4-dihydroxycyclopentane |
| 320 | 115 | 2-(4-methyl-6-carboxyhex-2-cis-enyl)-3-(2-hydroxyheptylthio]-1,4-dihydroxycyclopentane |
| 321 | 116 | 2-(4-methyl-6-carboxyhex-2-cis-enyl)-3-(2-hydroxyhexylthiol)-1,4-dihydroxycyclopentane |

EXAMPLE 322

Preparation of 5-(6-carboxyhex-2-cis-enyl)-7-(2,3,4a,6,7,7a-hexahydro)-6-oxo-2-pentyl-5H-cyclopenta[b]-1,4-oxathiin and 5-(6-carboxyhex-2cis-enyl)-4-(2-hydroxyheptylthio)cyclopent-2-en-1-one To a solution of 0.6 g. (1.61 mmol) of 2-(6-carboxyhex-2-cis-enyl)-3-(2-hydroxyheptylthio)-4-hydroxycyclopentanone in 20 ml. of tetrahydrofuran is added 11 ml. of 1.5N hydrochloric acid. After standing three days at room temperature, the mixture is poured into water and extracted with ether. The ether solution is dried over magnesium sulfate and the ether is removed at reduced pressure. The residue is chromatographed on two 2000 mu silica gel plates which are developed with ethyl acetate-benzene 1:1 containing 1% of acetic acid from the upper band is isolated 0.31 g. (0.87 mmol) of 5-(6-carboxyhex-2-cis-enyl)-7-(2,3,4a,6,7,7a-hexahydro)-6-oxo-2-pentyl-5H-cyclopenta[b]-1,4-oxathiin as a white solid mixture of two isomers.

MS: m/e, 354 (M+).

NMR: $\delta_{rms}^{CDCl_3}$, 5.42 (m, 2H, vinyl), 4.52 and 4.32 (m's, 1H, cyclopentyl protons α to oxygen in each isomer), 3.92 and 3.63 (m's, 1H, α to oxygen to each isomer), 3.20-1.90 (m's, 12H, allylic protons α to carbonyls and sulfur) 1.90-1.13 (m's, 10H, methylenes) 0.90 (m, 3H, terminal methyl), 8.90 (bs, 1H, CO$_2$H).

IR: neat, 1750 (ketone), 1713 (acid) cm$^{-1}$. From the lower band is isolated 0.10 g. (0.282 mmol) of 5-(6-carboxyhex-2-cis-enyl)-4-(2-hydroxyheptylthio)cyclopent-2-en-1-one as a light yellow oil.

NMR: $\delta_{rms}^{CDCl_3}$, 7.67 (dd, 1H, enone proton B to carbonyl, J=6.0, J=2.8 Hz), 6.30 (dd, 1H enone proton α to carbonyl, J=6.0, J=1.0 Hz), 7.11 (bs, 2H, OH's), 5.50 (m, 2H, vinyl), 3.78 (m, 2H, α to OH, cyclopentyl α to S), 3.30-1.67 (m's, 11H, protons α to S and carbonyls, allylic, B to acid), 1.67-1.12 (m, 8H, methylenes), 0.90 (m, 3H, terminal methyl).

IR: neat, 3500 (OH) 1710 (carbonyl), 1590 (enone double bond) cm$^{-1}$.

EXAMPLES 323-355

By the procedure described in Example 322, the various cyclopentenones and oxathiins listed in Table XI are prepared.

| Example | 4-hydroxycyclopentanone of Example | Products |
|---|---|---|
| 323 | 110 | 5-(6-carboxyhex-2-cis-enyl)-4-(2-hydroxyoctylthio)cyclopent-2-en-1-one and 5-(6-carboxyhex-2-cis-enyl)-7-(2,3,4a,6,7,7a-hexahydro)-6-oxo-2-hexyl-5H-cyclopenta[b]-1,4-oxathiin |
| 324 | 115 | 5-(4-methyl-6-carboxyhex-2-cis-enyl)-4-(2-hydroxyheptylthio)cyclopent-2-en-1-one and 5-(4-methyl-6-carboxyhex-2-cis-enyl)-7-(2,3,4a,6,7,7a-hexahydro)-6-oxo-2-pentyl-5H-cyclopenta[b]-1,4-oxathiin |
| 325 | 121 | (5-(4-propyl-6-carboxyhex-2-cis-enyl)-4-(2-hydroxyheptylthio)cyclopent-2-en-1-one- and 5-(4-propyl-6-carboxyhex-2-cis-enyl)-7-(2,3,4a,6,7,7a-hexahydro)-6-oxo-2-pentyl-5H-cyclopenta[b]-1,4-oxathiin |

-continued

| Example | 4-hydroxycyclopentanone of Example | Products |
|---|---|---|
| 326 | 127 | 5-(6-carboxy-5-oxahexyl)-4-(2-hydroxyheptylthio)cyclopent-2-en-1-one and 5-(6-carboxy-5-oxahexyl)-7-(2,3,4a,6,7,7a-hexahydro)-6-oxo-2-pentyl-5H-cyclopenta[b]-1,4-oxathiin |
| 327 | 133 | 5-(5,5-dimethyl-6-carboxyhexyl)-4-(2-hydroxyheptylthio)-cyclopent-2-en-1-one and 5-(5,5-dimethyl-6-carboxyhexyl)-7-(2,3,4a,6,7,7a-hexahydro)-6-oxo-2-pentyl-5H-cyclopenta[b]-1,4-oxathiin |
| 328 | 139 | 5-(5-carboxypent-2-cis-enyl)-4-(2-hydroxyheptylthio)-cyclopent-2-en-1-one and 5-(5-carboxypent-2-cis-enyl)-7-(2,3,4a,6,7,7a-hexahydro)-6-oxo-2-pentyl-5H-cyclopenta[b]-1,4-oxathiin |
| 329 | 146 | 5-(7-carboxyhept-2-cis-enyll)-4-(2-hydroxyoctylthio)cyclopent-2-en-1-one and 5-(7-carboxyhept-2-cis-enyl)-7-(2,3,4a,6,7,7a-hexahydro)-6-oxo-2-hexyl-5H-cyclopenta[b]-1,4-oxathiin |
| 330 | 151 | 5-(6-methyl-6-carboxyhexyl)-4-(2-hydroxyheptylthio)-cyclopent-2-en-1-one and 5-(6-methyl-6-carboxyhexyl)-7-(2,3,4a,6,7,7a-hexahydro)-6-oxo-2-pentyl-5H-cyclopenta[b]-1,4-oxathiin |
| 331 | 152 | 5-(6-methyl-6-carboxyhexyl)-4-(2-hydroxyhexylthio)cyclopent-2-en-1-one and 5-(6-methyl-6-carboxyhexyl)-7-(2,3,4a,6,7,7a-hexahydro)-6-oxo-2-butyl-5H-cyclopenta[b]-1,4-oxathiin |
| 332 | 157 | 5-(6-ethyl-6-carboxyhexyl)-4-(2-hydroxyheptylthio)cyclopent-2-en-1-one and 5-(6-ethyl-6-carboxyhexyl)-7-(2,3,4a,6,7,7a-hexahydro)-6-oxo-2-pentyl-5H-cyclopenta[b]-1,4-oxathiin |
| 333 | 186 | 5-(6-carbomethoxyhex-2-cis-enyl)-4-(2-hydroxyheptylthio)-cyclopent-2-en-1-one and 5-(6-carbomethoxyhex-2-cis-enyl)-7-(2,3,4a,6,7,7a-hexahydro)-6-oxo-2-pentyl-5H-cyclopenta[b]-1,4-oxathiin |
| 334 | 180 | 5-(5,5-dimethyl-6-carbomethoxyhexyl)-4-(2-hydroxyheptylthio)cyclopent-2-en-1-one and 5-(5,5-dimethyl-6-carbomethoxyhexyl)-7-(2,3,4a,6,7,7a-hexahydro)-6-oxo-2-pentyl-5H-cyclopenta[b]-1,4-oxathiin |
| 335 | 106 | 5-(6-carboxyhex-2-cis-enyl)-4-[2-hydroxy-3-(3-trifluoromethylphenoxy)propylthio]-cyclopent-2-en-1-one and 5-(6-carboxyhex-2-cis-enyl)-7-(2,3,4a,6,7,7a-hexahydro)-6-oxo-2-(3-trifluoromethylphenoxymethyl)-5H-cyclopenta[b]-1,4-oxathiin |
| 336 | 108 | 5-(6-carboxyhex-2-cis-enyl)-4-[2-hydroxy-3-(2-methylphenoxy)propylthio]cyclopent-2-en-1-one and 5-(6-carboxyhex-2-cis-enyl)-7-(2,3,4a,6,7,7a-hexahydro)-6-oxo-2-(2-methylphenoxymethyl)-5H-cyclopenta[b]-1,4-oxathiin |
| 337 | 109 | 5-(6-carboxyhex-2-cis-enyl)-4-[2-hydroxy-3-(4-fluorophenoxy)propylthio]cyclopent-2-en-1-one and 5-(6-carboxyhex-2-cis-enyl)-7-(2,3,4a,6,7,7a-hexahydro)-6-oxo-2-(4-fluorophenoxymethyl)-5H-cyclopenta[b]-1,4-oxathiin |
| 338 | 107 | 5-(6-carboxyhex-2-cis-enyl)-4-[2-hydroxy-3-(3-chlorophenoxy)propylthio]cyclopent-2-en-1-one and 5-(6-carboxyhex-2-cis-enyl)-7-(2,3,4a,6,7,7a-hexahydro)-6-oxo-2-(3-chlorophenoxymethyl)-5H-cyclopenta[b]-1,4-oxathiin |
| 339 | 111 | 5-(4-methyl-6-carboxyhex-2-cis-enyl)-4-[2-hydroxy-3-(4-fluorophenoxy)propylthio]cyclopent-2-en-1-one and 5-(4-methyl-6-carboxyhex-2-cis-enyl)-7-(2,3,4a,6,7,7a-hexahydro)-6-oxo-2-(4-fluorophenoxymethyl)-5H-cyclopenta[b]-1,4-oxathiin |
| 340 | 118 | 5-(4-propyl-6-carboxyhex-2-cis-enyl)-4-[2-hydroxy-3-(3-trifluoromethylphenoxy)-propylthio]cyclopent-2-en-1-one and 5-(4-propyl-6-carboxyhex-2-cis-enyl)-7-(2,3,4a,6,7,7a-hexahydro)-6-oxo-2-(3-trifluoromethylphenoxymethyl)-5H-cyclopenta[b]-1,4-oxathiin |
| 341 | 125 | 5-(6-carboxy-5-oxahexyl)-4-[2-hydroxy-3-(3-chlorophenoxy)propylthio]cyclopent-2-en-1-one and 5-(6-carboxy-5-oxahexyl)-7-(2,3,4a,6,7,7a-hexahydro)-6-oxo-2-(3-chlorophenoxymethyl)-5H-cyclopenta[b]-1,4-oxathiin |
| 342 | 129 | 5-(5,5-dimethyl-6-carboxyhexyl)-4-[2-hydroxy-3-(4-fluorophenoxy)propylthio]cyclopent-2-en-1-one and 5-(5,5-dimethyl-6-carboxyhexyl)-7-(2,3,4a,6,7,7a-hexahydro)-6-oxo-2-(4-fluorophenoxymethyl)-5H-cyclopenta[b]-1,4-oxathiin |
| 343 | 136 | 5-(5-carboxypent-2-cis-enyl)-4-[2-hydroxy-3-(3-trifluoromethylphenoxy)propylthio]cyclopent-2-en-1-one and 5-(carboxypent-2-cis-enyl)-7-(2,3,4a,6,7,7a-hexahydro)-6-oxo-2-(3-trifluoromethylphenoxymethyl)-5H-cyclopenta[b]-1,4-oxathiin |
| 344 | 143 | 5-(7-carboxyhept-2-cis-enyl)-4-[2-hydroxy-3-(3-chlorophenoxy)propylthio]cyclopent-2-en-1-one and 5-(7-carboxyhept-2-cis-enyl)-7-(2,3,4a,6,7,7a-hexahydro)-6-oxo- |

| Example | 4-hydroxycyclopentanone of Example | Products |
|---|---|---|
| 345 | 150 | 2-(3-chlorophenoxymethyl)-5H-cyclopenta[b]-1,4-oxathiin 5-(6-methyl-6-carboxyhexyl)-4-[2-hydroxy-3-(3,4-dichlorophenoxy)propylthio]cyclopent-2-en-1-one and 5-(6-methyl-6-carboxyhexyl)-7-(2,3,4a,6,7,7a-hexahydro)-6-oxo-2-(3,4-dichlorophenoxymethyl)-5H-cyclopenta[b]-1,4-oxathiin |
| 346 | 147 | 5-(6-methyl-6-carboxhexyl)-4-[2-hydroxy-3-(4-fluorophenoxy)propylthio]cyclopent-2-en-1-one and 5-(6-methyl-6-carboxyhexyl)-7-(2,3,4a,6,7,7a-hexahydro)-6-oxo-2-(4-fluorophenoxymethyl)-5H-cyclopenta[b]-1,4-oxathiin |
| 347 | 154 | 5-(6-ethyl-6-carboxyhexyl)-4-[2-hydroxy-3-(3-trifluoromethylphenoxy)propylthio]cyclopent-2-en-1-one and 5-(6-ethyl-6-carboxyhexyl)-7-(2,3,4a,6,7,7a-hexahydro)-6-oxo-2-(3-trifluoromethylphenoxymethyl)-5H-cyclopenta-[b]-1,4-oxathiin |
| 348 | 159 | 5-(6-carboxyhexyl)-4-[2-hydroxy-3-(4-fluorophenoxy)-propylthio]cyclopent-2-en-1-one and 5-(6-carboxyhexyl)-7-(2,3,4a,6,7,7a-hexahydro)-6-oxa-2-(4-fluorophenoxymethyl)-5H-cyclopenta[b]-1,4-oxathiin |
| 349 | 160 | 5-(6-carboxyhexyl)-4-[2-hydroxy-3-(3-trifluoromethylphenoxy)propylthio]cyclopent-2-en-1-one and 5-(6-carboxyhexyl)-7-(2,3,4a,6,7,7a-hexahydro)-6-oxo-2-(3-trifluoromethylphenoxymethyl)-5H-cyclopenta[b]-1,4-oxathiin |
| 350 | 165 | 5-(5-carboxypentyl)-4-[2-hydroxy-3-(3-chlorophenoxy)-propylthio]cyclopent-2-en-1-one and 5-(5-carboxypentyl)-7-(2,3,4a,6,7,7a-hexahydro)-6-oxa-2-(3-chlorophenoxymethyl)-5H-cyclopenta[b]-1,4-oxathiin |
| 351 | 167 | 5-(7-carboxyheptyl)-4-[2-hydroxy-3-(4-fluorophenoxy)-propylthio]cyclopent-2-en-1-one and 5-(7-carboxyheptyl)-7-(2,3,4a,6,7,7a-hexahydro)-6-oxa-2-(4-fluorophenoxymethyl)-5H-cyclopenta[b]-1,4-oxathiin |
| 352 | 173 | 5-(8-carboxyoctyl)-4-[2-hydroxy-3-(3-chlorophenoxy)propylthio]cyclopent-2-en-1-one and 5-(8-carboxyoctyl)-7-(2,3,4a,6,7,7a-hexahydro)-6-oxa-2-(3-chlorophenoxymethyl)-5H-cyclopenta[b]-1,4-oxathiin |
| 353 | 182 | 5-(6-carboxymethoxyhex-2-cis-enyl)-4-[2-hydroxy-3-(4-fluorophenoxy)propylthio]cyclopent-2-en-1-one and 5-(6-carbomethoxyhex-2-cis-enyl)-7-(2,3,4a,6,7,7a-hexahydro)-6-oxa-2-(4-fluorophenoxymethyl)-5H-cyclopenta-[b]-1,4-oxathiin |
| 354 | 188 | 5-(6-methyl-6-carbomethoxyhexyl)-4-[2-hydroxy-3-(4-fluorophenoxy)propylthio]cyclopent-2-en-1-one and 5-(6-methyl-6-carbomethoxyhexyl)-7-(2,3,4a,6,7,7a-hexahydro)-6-oxa-2-(4-fluorophenoxymethyl)-5H-cyclopenta[b]-1,4-oxathiin |
| 355 | 120 | 5-(6-carboxyhex-2-cis-enyl)-4-[2-hydroxy-3-(4-chlorophenoxy)propylthio]cyclopent-2-en-1-one and 5-(6-carboxyhex-2-cis-enyl)-7-(2,3,4a,6,7,7a-hexahydro)-6-oxo-2-(4-chlorophenoxymethyl)-5H-cyclopenta[b]-1,4-oxathiin |

I claim:

1. A compound selected from the group consisting of an optically active compound of the formula:

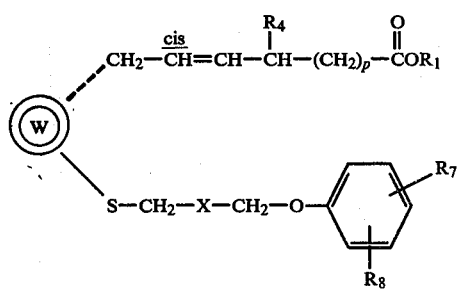

and a racemic compound of that formula and the mirror image thereof, wherein w is selected from the group consisting of:

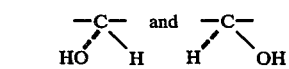

; $R_1$ is selected from the group consisting of hydrogen and alkyl having from 1 to 12 carbon atoms; $R_7$ and $R_8$ are each individually selected from the group consisting of hydrogen, halogen, alkyl having up to 3 carbon atoms and trifluoromethyl; X is a divalent radical selected from the group consisting of those of the formulae:

$$-\underset{HO}{\overset{}{C}}-\underset{H}{\overset{}{\phantom{C}}} \quad \text{and} \quad -\underset{H}{\overset{}{C}}-\underset{OH}{\overset{}{\phantom{C}}}$$

$R_4$ is hydrogen or alkyl having up to 3 carbon atoms, and p is an integer from 2 to 5 inclusive; and the pharmacological acceptable salts thereof when $R_1$ is hydrogen.

2. A compound according to claim 1, wherein $R_4$ is hydrogen and p is one.

3. The optically active compound according to claim 1 wherein $R_1$ is hydrogen, $R_2$ is hydrogen, $R_3$ is 4-fluorophenoxymethyl, X is

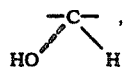

Y is

and Z is

l-2α-(6-carboxyhex-2-cis-enyl)-3β-[2(S)-hydroxy-3-(4-fluorophenoxy)propylthio]cyclopentanone.

4. The racemic compound according to claim 1 wherein $R_1$ is hydrogen, $R_2$ is hydrogen, $R_3$ is 4-fluorophenoxymethyl, X is

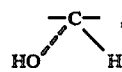

Y is

and Z is

dl-2α-(6-carboxyhex-2-cis-enyl)-3β-[2(S)-hydroxy-3-(4-fluorophenoxy)propylthio]cyclopentanone.

5. The optically active compound according to claim 1, wherein $R_1$ is hydrogen, $R_2$ is hydrogen, $R_3$ is 3-trifluoromethylphenoxymethyl, X is

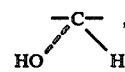

Y is

and Z is

l-2α-(6-carboxyhex-2-cis-enyl)-3β-]2(S)-hydroxy-3-(3-trifluoromethylphenoxy)propylthio]cyclopentanone.

6. The racemic compound according to claim 1 wherein $R_1$ is hydrogen, $R_2$ is hydrogen, $R_3$ is 3-trifluoromethylphenoxymethyl, X is

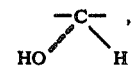

Y is

and Z is

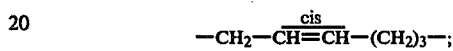

dl-2α-(6-carboxyhex-2-cis-enyl)-3β-[2(S)-hydroxy-3-(3-trifluoromethylphenoxy)propylthio]cyclopentanone.

7. The optically active compound according to claim 1 wherein $R_1$ is hydrogen, $R_2$ is hydrogen, $R_3$ is 3-chlorophenoxymethyl, X is

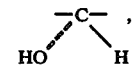

Y is

and Z is

l-2α-(6-carboxyhex-2-cis-enyl)-3β-[2(S)-hydroxy-3-(3-chlorophenoxy)propylthio]cyclopentanone.

8. The racemic compound according to claim 1 wherein $R_1$ is hydrogen, $R_2$ is hydrogen, $R_3$ is 3-chlorophenoxymethyl, X is

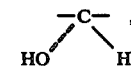

Y is

and Z is

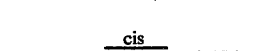

dl-2α-(6-carboxyhex-2-cis-enyl)-3β-[2(S)-hydroxy-3-(3-chlorophenoxy)propylthio]cyclopentanone.

* * * * *